US012011308B2

(12) United States Patent
Cao et al.

(10) Patent No.: US 12,011,308 B2
(45) Date of Patent: Jun. 18, 2024

(54) IMAGING SYSTEM

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

( * ) Notice: Subject to any disclaimer, the term of this patent is extended or adjusted under 35 U.S.C. 154(b) by 620 days.

(21) Appl. No.: 17/179,498

(22) Filed: Feb. 19, 2021

(65) Prior Publication Data
US 2021/0169434 A1     Jun. 10, 2021

Related U.S. Application Data

(63) Continuation of application No. PCT/CN2018/106887, filed on Sep. 21, 2018.

(51) Int. Cl.
*G06T 7/00* (2017.01)
*A61B 6/00* (2006.01)

(52) U.S. Cl.
CPC .......... *A61B 6/5241* (2013.01); *A61B 6/5223* (2013.01); *A61B 6/547* (2013.01); *G06T 7/0012* (2013.01); *G06T 2207/30204* (2013.01)

(58) Field of Classification Search
None
See application file for complete search history.

(56) References Cited

U.S. PATENT DOCUMENTS

| 8,139,255 | B2 * | 3/2012 | Matsunaga | ........ H04N 1/40068 |
| | | | | 358/1.16 |
| 8,184,773 | B2 * | 5/2012 | Cheng | ................. A61N 5/1069 |
| | | | | 378/65 |
| 8,269,195 | B2 * | 9/2012 | Rigney | ................ A61N 5/1049 |
| | | | | 378/68 |
| 8,488,735 | B2 * | 7/2013 | Fujita | ................... H04N 25/622 |
| | | | | 378/19 |

(Continued)

FOREIGN PATENT DOCUMENTS

| CN | 1894577 A | 1/2007 |
| CN | 101933143 A | 12/2010 |

(Continued)

*Primary Examiner* — David P Porta
*Assistant Examiner* — Djura Malevic
(74) *Attorney, Agent, or Firm* — IPRO, PLLC; Qian Gu

(57) ABSTRACT

Disclosed herein is a system comprising: a radiation source; a marker; a first image sensor; and a second image sensor; wherein the first image sensor is configured to capture images of the marker; wherein the second image sensor is configured to move between a first position and a second position; wherein the second image sensor is configured to capture a first set of images of portions of a scene at the first position and to capture a second set of images of portions of the scene at the second position; wherein the second image sensor and the radiation source are configured to collectively rotate relative to the scene; wherein the second image sensor is configured to form an image of the scene by stitching an image selected from the first set and an image selected from the second set based on the images of the marker.

28 Claims, 25 Drawing Sheets

(56) References Cited

U.S. PATENT DOCUMENTS

| | | | | |
|---|---|---|---|---|
| 8,633,445 B2* | 1/2014 | Star-Lack | A61B 6/5282 | 250/363.04 |
| 8,675,813 B2* | 3/2014 | Fujita | G01T 1/247 | 378/19 |
| 8,750,453 B2* | 6/2014 | Cheng | A61N 5/1069 | 378/68 |
| 8,891,732 B2* | 11/2014 | Wu | G03F 9/7065 | 378/205 |
| 8,899,832 B2* | 12/2014 | Fabrizio | A61B 6/06 | 378/208 |
| 8,981,324 B2* | 3/2015 | Rigney | B25J 9/1666 | 378/68 |
| 9,084,886 B2* | 7/2015 | Bush | A41C 3/00 | |
| 9,220,922 B2* | 12/2015 | Morrow | A61N 5/1049 | |
| 9,322,938 B2* | 4/2016 | Kämmerer | G01T 1/2985 | |
| 9,459,217 B2* | 10/2016 | Wang | G06T 3/4069 | |
| 9,513,385 B2* | 12/2016 | Cox | G01T 1/243 | |
| 9,579,071 B2* | 2/2017 | Lee | A61B 6/022 | |
| 9,974,498 B2* | 5/2018 | Humphrey | G01T 1/20185 | |
| 9,976,971 B2* | 5/2018 | Cernatescu | G01N 23/20008 | |
| 10,007,009 B2* | 6/2018 | Cao | G01T 1/247 | |
| 10,029,122 B2* | 7/2018 | Michaud | A61N 5/1049 | |
| 10,098,609 B2* | 10/2018 | Kim | A61B 6/4464 | |
| 10,434,339 B2* | 10/2019 | Pencea | A61N 5/1081 | |
| 10,448,914 B2* | 10/2019 | Spahn | A61B 6/482 | |
| 10,502,843 B2* | 12/2019 | Cao | G01T 1/247 | |
| 10,583,312 B2* | 3/2020 | Ono | A61N 5/1081 | |
| 10,588,591 B2* | 3/2020 | Sano | A61B 6/484 | |
| 10,705,031 B2* | 7/2020 | Cao | G21K 7/00 | |
| 10,874,362 B2* | 12/2020 | Benson | H01J 35/02 | |
| 10,881,362 B2* | 1/2021 | Nayak K | A61B 6/40 | |
| 10,925,561 B2* | 2/2021 | Snow | A61B 6/4405 | |
| 10,939,884 B2* | 3/2021 | Nariyuki | A61B 6/461 | |
| 10,952,689 B2* | 3/2021 | Cox | A61B 6/4208 | |
| 11,009,614 B2* | 5/2021 | Cao | G01T 1/247 | |
| 11,051,774 B2* | 7/2021 | Bothorel | A61B 6/06 | |
| 11,160,515 B2* | 11/2021 | Yoshimura | A61B 6/4435 | |
| 11,382,579 B2* | 7/2022 | Shimizukawa | A61B 6/461 | |
| 11,382,582 B1* | 7/2022 | Ruff | A61B 6/4405 | |
| 11,534,251 B2* | 12/2022 | Nowlin | A61B 34/30 | |
| 11,543,543 B2* | 1/2023 | Kawata | G01T 1/17 | |
| 11,559,265 B2* | 1/2023 | Xu | A61B 6/027 | |
| 11,650,050 B2* | 5/2023 | Rees | G01B 21/042 | 702/85 |
| 11,684,330 B2* | 6/2023 | Ruff | A61B 6/4405 | 378/98.2 |
| 11,686,791 B2* | 6/2023 | Klomp | G01R 33/34007 | 324/322 |
| 11,717,700 B2* | 8/2023 | O'Neal, III | H05H 7/04 | 250/492.3 |
| 11,717,703 B2* | 8/2023 | Cooley | A61N 5/1079 | 250/492.3 |
| 2009/0067577 A1* | 3/2009 | Rigney | G05B 15/02 | 378/65 |
| 2010/0166140 A1* | 7/2010 | Proksa | A61B 6/032 | 382/131 |
| 2010/0192303 A1* | 8/2010 | Miller | A61N 5/1037 | 5/624 |
| 2010/0246755 A1* | 9/2010 | Suzuki | A61B 6/4441 | 378/11 |
| 2011/0019795 A1* | 1/2011 | Fujita | H01L 27/14656 | 378/19 |
| 2011/0188726 A1* | 8/2011 | Nathaniel | A61B 6/4441 | 378/42 |
| 2011/0226951 A1* | 9/2011 | Kammerer | G01T 1/2985 | 250/336.1 |
| 2012/0039435 A1* | 2/2012 | Arai | A61B 6/542 | 378/11 |
| 2012/0176406 A1* | 7/2012 | Elenbaas | A61B 6/5241 | 345/629 |
| 2012/0189096 A1* | 7/2012 | Erhardt | A61B 6/4233 | 378/22 |
| 2012/0224667 A1* | 9/2012 | Cheng | A61N 5/1067 | 378/20 |
| 2012/0307963 A1* | 12/2012 | Watanabe | G21K 1/025 | 378/7 |
| 2012/0323516 A1* | 12/2012 | Rigney | A61N 5/1037 | 702/94 |
| 2013/0083890 A1* | 4/2013 | Wu | G03F 9/7065 | 378/62 |
| 2013/0101088 A1* | 4/2013 | Fabrizio | A61B 6/08 | 378/205 |
| 2013/0114789 A1* | 5/2013 | Barbato | A61B 6/4233 | 378/62 |
| 2013/0136226 A1* | 5/2013 | Tomoe | A61B 6/14 | 378/4 |
| 2013/0279650 A1* | 10/2013 | Fujita | H01L 27/14656 | 378/19 |
| 2014/0126687 A1* | 5/2014 | Yoshikawa | A61B 6/469 | 378/39 |
| 2014/0323851 A1* | 10/2014 | Barberi | A61B 6/0428 | 5/622 |
| 2015/0032233 A1* | 1/2015 | Cheng | A61N 5/107 | 700/90 |
| 2015/0146854 A1* | 5/2015 | Barbato | G01T 1/20185 | 378/62 |
| 2015/0177391 A1* | 6/2015 | Cox | G01N 23/04 | 378/62 |
| 2015/0213633 A1* | 7/2015 | Chang | A61B 6/032 | 382/284 |
| 2015/0251019 A1* | 9/2015 | Rigney | A61N 5/1078 | 600/1 |
| 2015/0260859 A1* | 9/2015 | Christoph | G06T 11/008 | 378/207 |
| 2016/0047759 A1* | 2/2016 | Wang | G01N 23/046 | 378/11 |
| 2016/0143609 A1* | 5/2016 | Park | A61B 6/587 | 378/98.2 |
| 2016/0166230 A1* | 6/2016 | Kim | A61B 6/465 | 378/205 |
| 2016/0287907 A1* | 10/2016 | Michaud | A61N 5/107 | |
| 2017/0038484 A1* | 2/2017 | Cox | G21K 1/046 | |
| 2017/0087389 A1* | 3/2017 | Benner | A61N 5/1082 | |
| 2017/0176609 A1* | 6/2017 | Tsubota | G01N 23/046 | |
| 2017/0341183 A1* | 11/2017 | Buller | B22F 10/36 | |
| 2017/0367664 A1* | 12/2017 | Xi | A61B 6/5241 | |
| 2018/0017686 A1* | 1/2018 | Cao | G01T 1/247 | |
| 2018/0117361 A1* | 5/2018 | Pencea | G01T 1/29 | |
| 2018/0156927 A1* | 6/2018 | Cao | G01T 1/247 | |
| 2018/0264287 A1* | 9/2018 | Ono | A61N 5/1069 | |
| 2018/0368799 A1* | 12/2018 | Sano | A61B 6/5264 | |
| 2019/0223826 A1* | 7/2019 | Asano | A61B 6/40 | |
| 2019/0307415 A1* | 10/2019 | Antikainen | A61B 6/0492 | |
| 2020/0008761 A1* | 1/2020 | Yoshimura | A61B 6/04 | |
| 2020/0072986 A1* | 3/2020 | Cao | G01T 1/247 | |
| 2021/0169434 A1* | 6/2021 | Cao | A61B 6/4266 | |
| 2021/0185203 A1* | 6/2021 | Cao | G01V 5/0066 | |
| 2022/0003886 A1* | 1/2022 | Kawata | G01T 1/24 | |
| 2023/0010663 A1* | 1/2023 | Cao | A61B 6/4007 | |

FOREIGN PATENT DOCUMENTS

| | | |
|---|---|---|
| CN | 103035547 A | 4/2013 |
| CN | 104937370 A | 9/2015 |
| CN | 108020856 A | 5/2018 |
| CN | 108474661 A | 8/2018 |
| JP | 2001176941 A | 6/2001 |
| JP | 2014025763 A | 2/2014 |

* cited by examiner

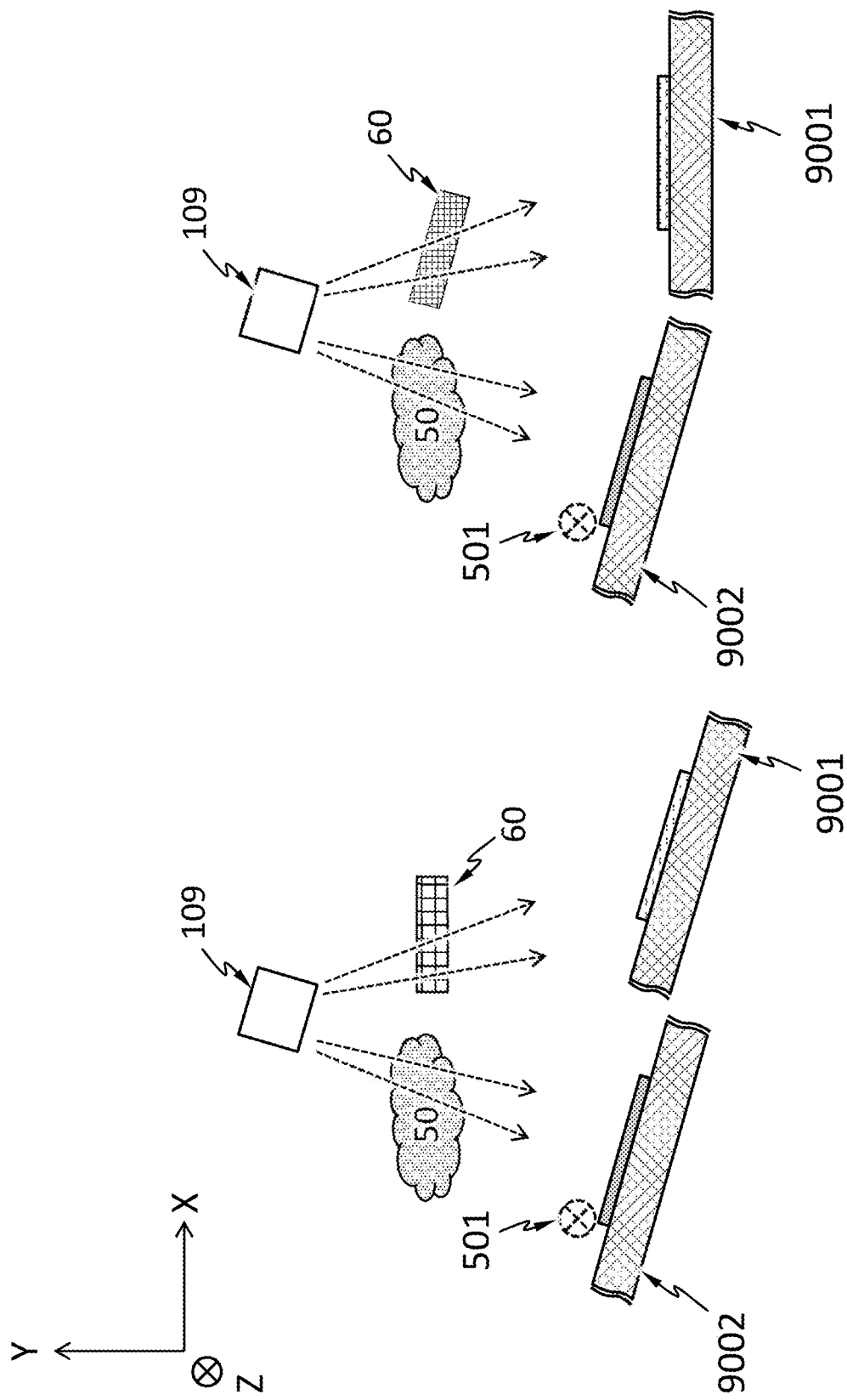

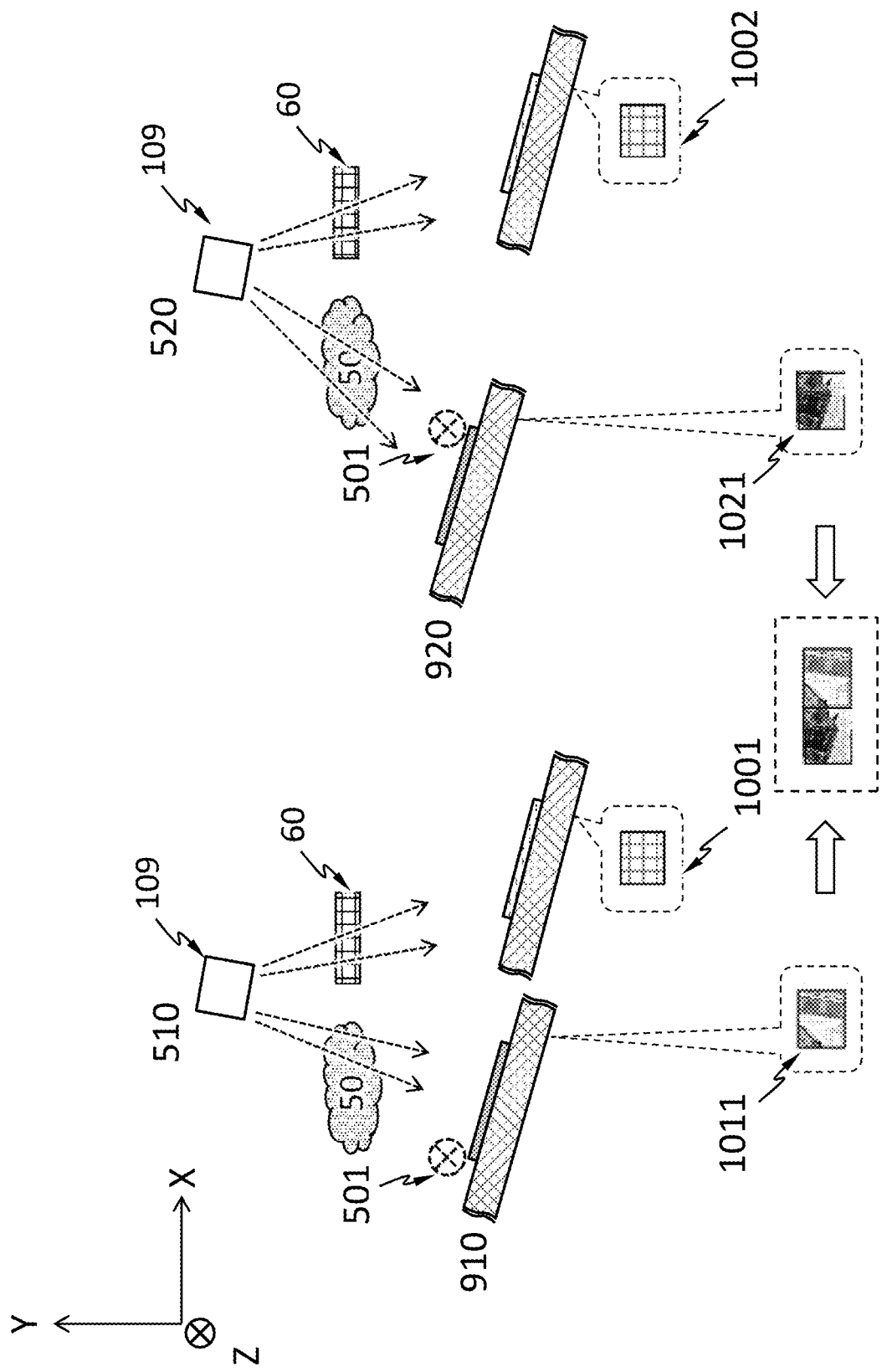

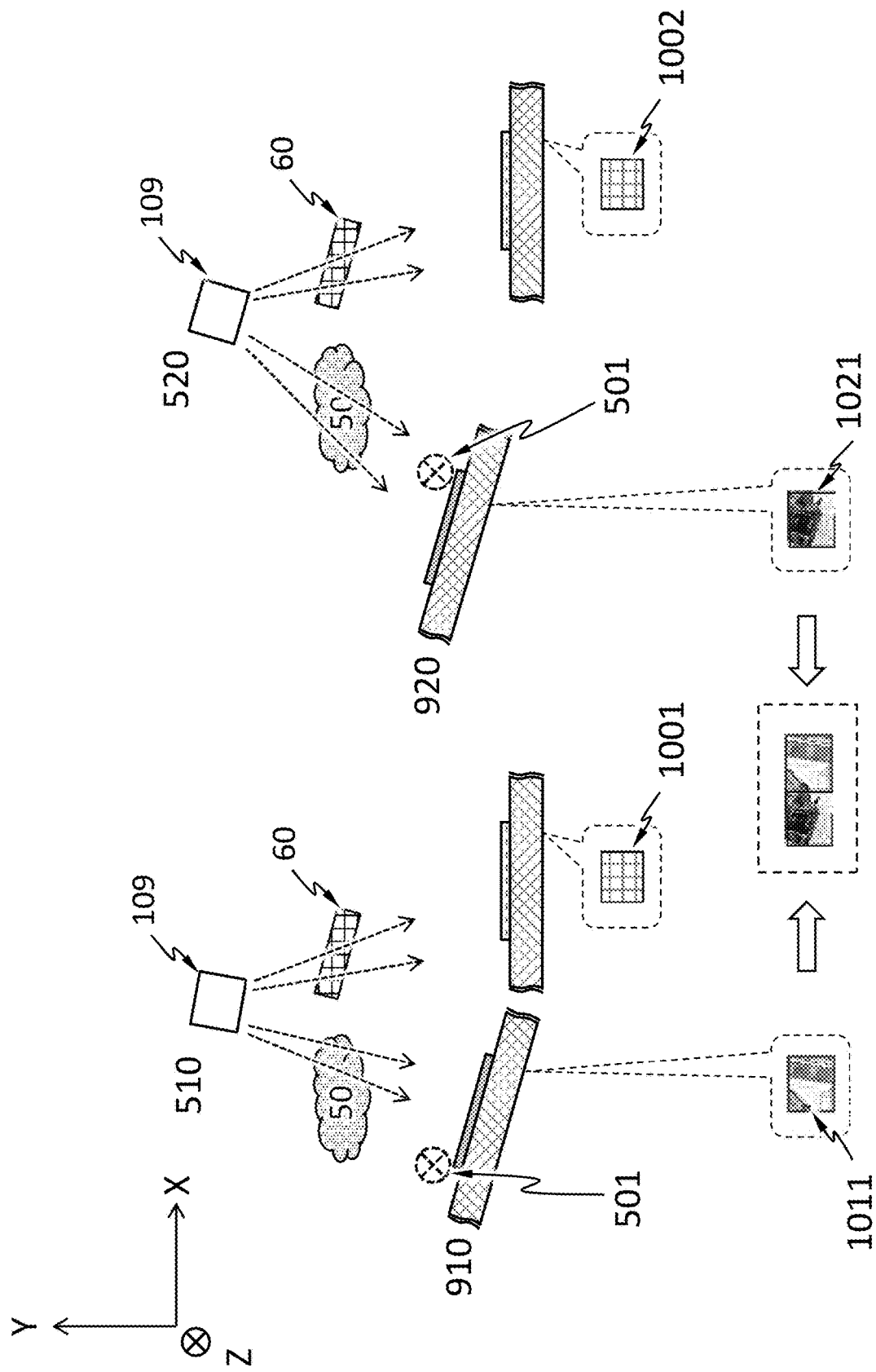

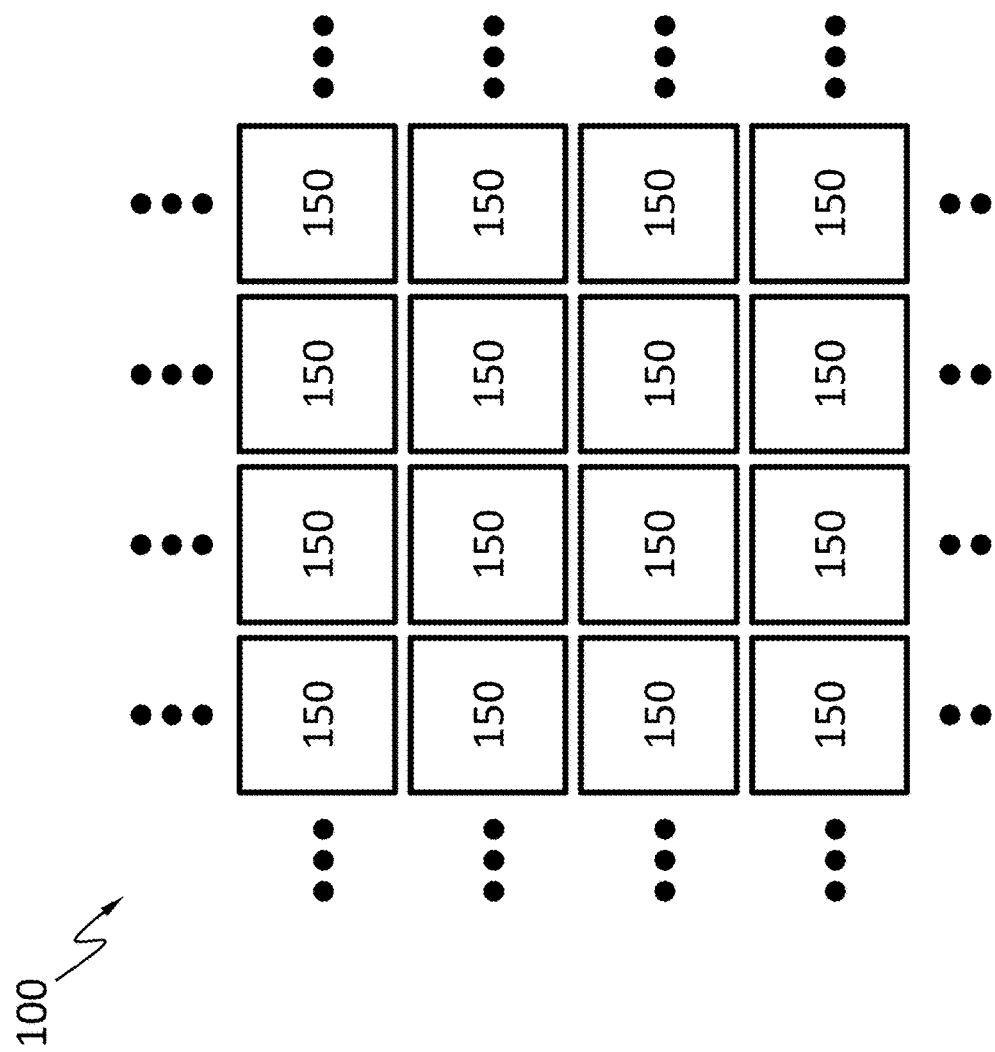

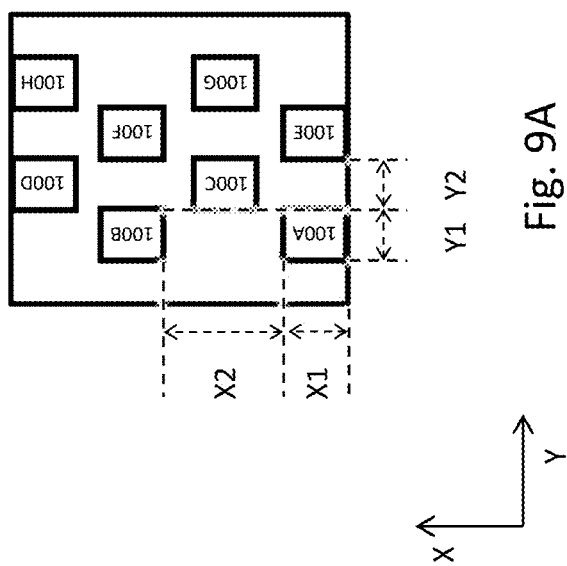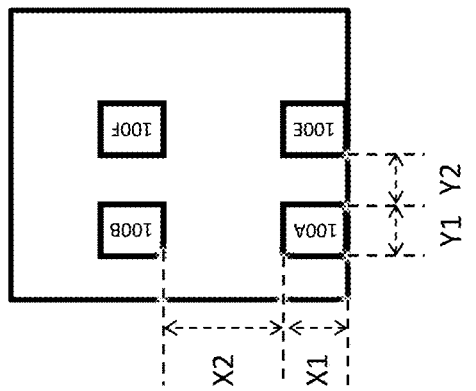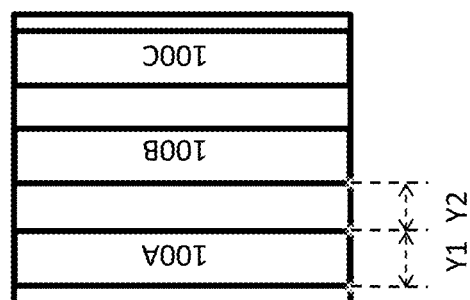
Fig. 9A
Fig. 9B
Fig. 9C

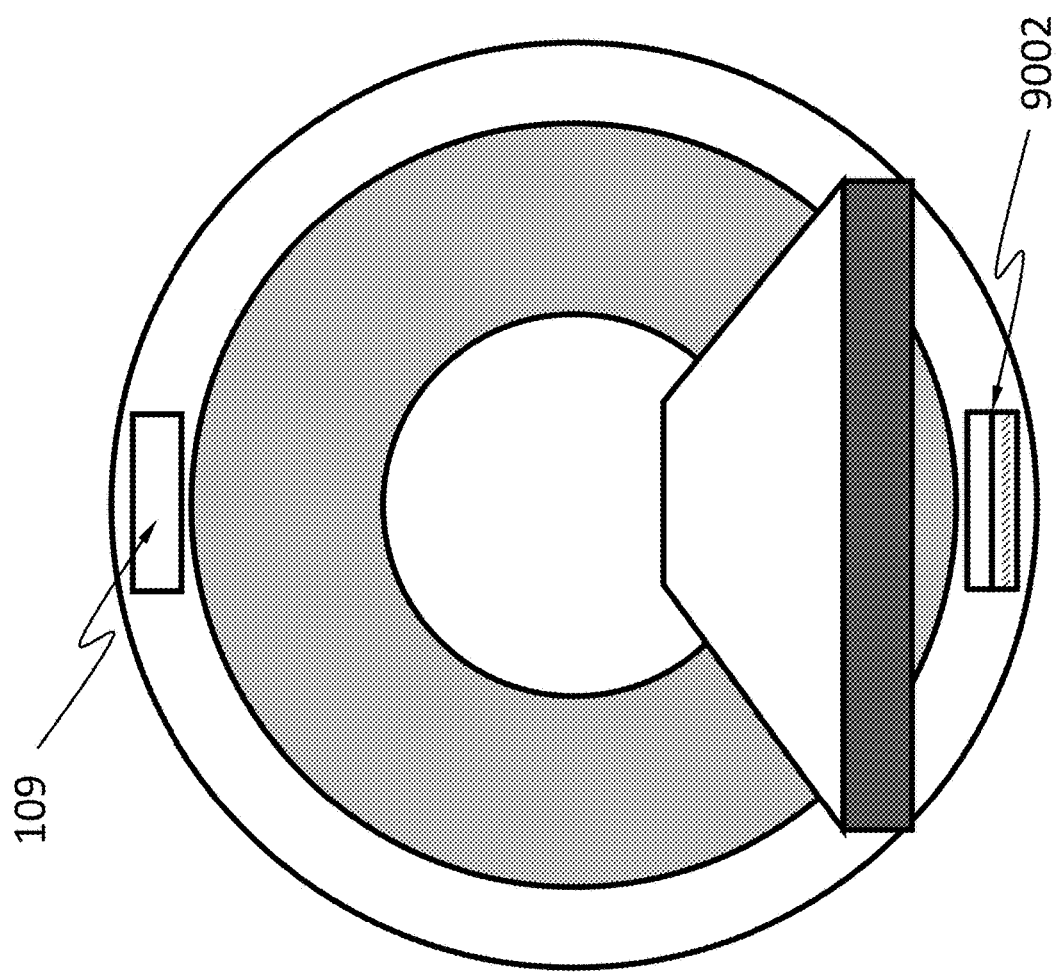

IMAGING SYSTEM

BACKGROUND

Radiation detectors may be devices used to measure the flux, spatial distribution, spectrum or other properties of radiations.

Radiation detectors may be used for many applications. One important application is imaging. Radiation imaging is a radiography technique and can be used to reveal the internal structure of a non-uniformly composed and opaque object such as the human body.

Early radiation detectors for imaging include photographic plates and photographic films. A photographic plate may be a glass plate with a coating of light-sensitive emulsion. Although photographic plates were replaced by photographic films, they may still be used in special situations due to the superior quality they offer and their extreme stability. A photographic film may be a plastic film (e.g., a strip or sheet) with a coating of light-sensitive emulsion.

In the 1980s, photostimulable phosphor plates (PSP plates) became available. A PSP plate may contain a phosphor material with color centers in its lattice. When the PSP plate is exposed to radiation, electrons excited by radiation are trapped in the color centers until they are stimulated by a laser beam scanning over the plate surface. As the plate is scanned by laser, trapped excited electrons give off light, which is collected by a photomultiplier tube. The collected light is converted into a digital image. In contrast to photographic plates and photographic films, PSP plates can be reused.

Another kind of radiation detectors are radiation image intensifiers. Components of a radiation image intensifier are usually sealed in a vacuum. In contrast to photographic plates, photographic films, and PSP plates, radiation image intensifiers may produce real-time images, i.e., do not require post-exposure processing to produce images. Radiation first hits an input phosphor (e.g., cesium iodide) and is converted to visible light. The visible light then hits a photocathode (e.g., a thin metal layer containing cesium and antimony compounds) and causes emission of electrons. The number of emitted electrons is proportional to the intensity of the incident radiation. The emitted electrons are projected, through electron optics, onto an output phosphor and cause the output phosphor to produce a visible-light image.

Scintillators operate somewhat similarly to radiation image intensifiers in that scintillators (e.g., sodium iodide) absorb radiation and emit visible light, which can then be detected by a suitable image sensor for visible light. In scintillators, the visible light spreads and scatters in all directions and thus reduces spatial resolution. Reducing the scintillator thickness helps to improve the spatial resolution but also reduces absorption of radiation. A scintillator thus has to strike a compromise between absorption efficiency and resolution.

Semiconductor radiation detectors largely overcome this problem by direct conversion of radiation into electric signals. A semiconductor radiation detector may include a semiconductor layer that absorbs radiation in wavelengths of interest. When a radiation particle is absorbed in the semiconductor layer, multiple charge carriers (e.g., electrons and holes) are generated and swept under an electric field towards electric contacts on the semiconductor layer. Cumbersome heat management required in currently available semiconductor radiation detectors (e.g., Medipix) can make a detector with a large area and a large number of pixels difficult or impossible to produce.

SUMMARY

Disclosed herein is a system comprising: a radiation source; a marker; a first image sensor; and a second image sensor; wherein the first image sensor is configured to capture images of the marker; wherein the second image sensor is configured to move between a first position relative to the radiation source and a second position relative to the radiation source; wherein the second image sensor is configured to capture, with radiation from the radiation source, a first set of images of portions of a scene when the second image sensor is at the first position relative to the radiation source; wherein the second image sensor is configured to capture, with the radiation from the radiation source, a second set of images of portions of the scene when the second image sensor is at the second position relative to the radiation source; wherein the second image sensor and the radiation source are configured to collectively rotate relative to the scene; wherein the second image sensor is configured to form an image of the scene by selecting an image from the first set based on the images of the marker and selecting an image from the second set based on the images of the marker, and stitching the image selected from the first set and the image selected from the second set.

According to an embodiment, the marker is stationary relative to the scene; and wherein a relative position of the first image sensor with respect to the radiation source is fixed.

According to an embodiment, the first image sensor is stationary relative to the scene; and wherein a relative position of the marker with respect to the radiation source is fixed.

According to an embodiment, the second image sensor is configured to move between the first position relative to the radiation source and the second position relative to the radiation source by translating along a first direction relative to the radiation source.

According to an embodiment, the first direction is parallel to a radiation-receiving surface of the image sensor.

According to an embodiment, the second image sensor is configured to move between the first position relative to the radiation source and the second position relative to the radiation source by translating along a second direction relative to the radiation source; wherein the second direction is different from the first direction.

According to an embodiment, the second image sensor is configured to move between the first position relative to the radiation source relative to the radiation source by rotating about a first axis relative to the radiation source.

According to an embodiment, the second image sensor is configured to move between the first position relative to the radiation source and the second position relative to the radiation source by rotating about a second axis relative to the radiation source; wherein the second axis is different from the first axis.

According to an embodiment, the radiation source is on the first axis.

According to an embodiment, the second image sensor and the radiation source are configured to collectively rotate relative to the scene about one or more axes.

According to an embodiment, at least one of the one or more axes is on the second image sensor.

According to an embodiment, a first rotational position which the radiation source is at when the image selected from the first set is captured and a second rotational position which the radiation source is at when the image selected from the second set is captured are the same.

According to an embodiment, the images of the marker comprise a first image of the marker and a second image of the marker; wherein rotational positions which the radiation source is at when the image selected from the first set is captured and when the first image of the marker is captured are the same; wherein rotational positions which the radiation source is at when the image selected from the second set is captured and when the second image of the marker is captured are the same; wherein the first image of the marker and the second image of the marker are identical.

According to an embodiment, the second image sensor comprises a first radiation detector and a second radiation detector.

According to an embodiment, the first radiation detector and the second radiation detector respectively comprise a planar surface configured to receive the radiation; wherein the planar surface of the first radiation detector and the planar surface of the second radiation detector are not coplanar.

According to an embodiment, the first radiation detector and the second radiation detector are configured to move relative to the radiation source by translating along a first direction relative to the radiation source.

According to an embodiment, the first direction is parallel to the planar surface of the first radiation detector but not parallel to the planar surface of the second radiation detector.

According to an embodiment, the first radiation detector and the second radiation detector are configured to move relative to the radiation source by translating along a second direction relative to the radiation source; wherein the second direction is different from the first direction.

According to an embodiment, the first radiation detector and the second radiation detector are configured to move relative to the radiation source by rotating about a first axis relative to the radiation source.

According to an embodiment, the first radiation detector and the second radiation detector are configured to move relative to the radiation source by rotating about a second axis relative to the radiation source; wherein the second axis is different from the first axis.

According to an embodiment, the radiation source is on the first axis.

Disclosed herein is a system comprising: a radiation source; a marker; a first image sensor; and a second image sensor; wherein the second image sensor is configured to move between a first position relative to the radiation source and a second position relative to the radiation source; wherein the second image sensor is configured to capture, with radiation from the radiation source, an image of first portions of a scene, when the second image sensor is at the first position relative to the radiation source and the first image sensor captures a first image of the marker that matches one of a set of reference images; wherein the second image sensor is configured to capture, with the radiation from the radiation source, an image of second portions of the scene, when the second image sensor is at the second position relative to the radiation source and the first image sensor captures a second image of the marker that matches one of the set of reference images; wherein the second image sensor and the radiation source are configured to collectively rotate relative to the scene; wherein the second image sensor is configured to form an image of the scene by stitching the image of the first portions and the image of the second portions if the first image of the marker and the second image of the marker are identical.

According to an embodiment, the marker is stationary relative to the scene; and wherein a relative position of the first image sensor with respect to the radiation source is fixed.

According to an embodiment, the first image sensor is stationary relative to the scene; and wherein a relative position of the marker with respect to the radiation source is fixed.

According to an embodiment, the second image sensor is configured to move between the first position relative to the radiation source and the second position relative to the radiation source by translating along a first direction relative to the radiation source.

According to an embodiment, the first direction is parallel to a radiation-receiving surface of the image sensor.

According to an embodiment, the second image sensor is configured to move between the first position relative to the radiation source and the second position relative to the radiation source by translating along a second direction relative to the radiation source; wherein the second direction is different from the first direction.

According to an embodiment, the second image sensor is configured to move between the first position relative to the radiation source and the second position relative to the radiation source by rotating about a first axis relative to the radiation source.

According to an embodiment, the second image sensor is configured to move between the first position relative to the radiation source and the second position relative to the radiation source by rotating about a second axis relative to the radiation source; wherein the second axis is different from the second axis.

According to an embodiment, the radiation source is on the first axis.

According to an embodiment, the second image sensor and the radiation source are configured to collectively rotate relative to the scene about one or more axes.

According to an embodiment, at least one of the one or more axes is on the second image sensor.

According to an embodiment, a first rotational position which the radiation source is at when the first image of the marker is captured and a second rotational position which the radiation source is at when the second image of the marker is captured are the same.

According to an embodiment, the second image sensor is configured to determine the first rotational position based on the first image of the marker.

According to an embodiment, the second image sensor comprises a first radiation detector and a second radiation detector.

According to an embodiment, the first radiation detector and the second radiation detector respectively comprise a planar surface configured to receive the radiation; wherein the planar surface of the first radiation detector and the planar surface of the second radiation detector are not coplanar.

According to an embodiment, the first radiation detector and the second radiation detector are configured to move relative to the radiation source by translating along a first direction relative to the radiation source.

According to an embodiment, the first direction is parallel to the planar surface of the first radiation detector but not parallel to the planar surface of the second radiation detector.

According to an embodiment, the first radiation detector and the second radiation detector are configured to move relative to the radiation source by translating along a second direction relative to the radiation source; wherein the second direction is different from the first direction.

According to an embodiment, the first radiation detector and the second radiation detector are configured to move relative to the radiation source by rotating about a first axis relative to the radiation source.

According to an embodiment, the first radiation detector and the second radiation detector are configured to move relative to the radiation source by rotating about a second axis relative to the radiation source; wherein the second axis is different from the first axis.

According to an embodiment, the radiation source is on the first axis.

Disclosed herein is a method comprising when a radiation source is at a first rotational position relative to a scene, capturing an image of first portions of the scene with radiation from the radiation source and capturing a first image of a marker; when the radiation source is at a second rotational position relative to the scene, capturing an image of second portions of the scene with the radiation from the radiation source and capturing a second image of the marker; determining whether the first rotational position and the second rotational position are the same based on the first image of the marker and the second image of the marker; upon determining that the first rotational position and the second rotational position are the same, forming an image of the scene by stitching the image of the first portions and the image of the second portions.

According to an embodiment, the marker is stationary relative to the scene; wherein the first image of the marker and the second image of the marker are captured by a first image sensor whose relative position with respect to the radiation source is fixed.

According to an embodiment, the first image of the marker and the second image of the marker are captured by a first image sensor that is stationary relative to the scene; wherein a relative position of the marker with respect to the radiation source is fixed.

According to an embodiment, the image of the first portions of the scene is captured by a second image sensor when the second image sensor is at a first position relative to the radiation source; wherein the image of the second portions of the scene is captured by the second image sensor when the second image sensor is at a second position relative to the radiation source.

According to an embodiment, the second image sensor and the radiation source are configured to collectively rotate relative to the scene.

According to an embodiment, determining whether the first rotational position and the second rotational position are the same based on the first image of the marker and the second image of the marker comprises: determining the first rotational position based on the first image of the marker and determining the second rotational position based on the first image of the marker.

According to an embodiment, determining whether the first rotational position and the second rotational position are the same based on the first image of the marker and the second image of the marker comprises: determining whether the first image of the marker and the second image of the marker are identical.

Disclosed herein is a method comprising when a first image of a marker is captured and matches one of a set of reference images, capturing, with radiation from a radiation source, an image of first portions of a scene; when a second image of a marker is captured and matches one of a set of reference images, capturing, with the radiation from the radiation source, an image of second portions of the scene; determining whether the first image of the marker and the second image of the marker are identical; upon determining that the first image of the marker and the second image of the marker are identical, forming an image of the scene by stitching the image of the first portions and the image of the second portions.

According to an embodiment, the marker is stationary relative to the scene; wherein the first image of the marker and the second image of the marker are captured by a first image sensor whose relative position with respect to the radiation source is fixed.

According to an embodiment, the first image of the marker and the second image of the marker are captured by a first image sensor that is stationary relative to the scene; wherein a relative position of the marker with respect to the radiation source is fixed.

According to an embodiment, the image of the first portions of the scene is captured by a second image sensor when the second image sensor is at a first position relative to the radiation source; wherein the image of the second portions of the scene is captured by the second image sensor when the second image sensor is at a second position relative to the radiation source.

According to an embodiment, the second image sensor and the radiation source are configured to collectively rotate relative to the scene.

According to an embodiment, a first rotational position which the radiation source is at when the first image of the marker is captured and a second rotational position which the radiation source is at when the second image of the marker is captured are the same.

BRIEF DESCRIPTION OF FIGURES

FIG. 2A and FIG. 2B each schematically show movement of the marker and the first image sensor in the system of FIG. 1A, when the second image sensor and the radiation source in the system of FIG. 1A are collectively rotated relative to the scene, according to an embodiment.

FIG. 3A and FIG. 3B each schematically show operation of the system, according to an embodiment.

FIG. 4A and FIG. 4B schematically show operation of the system, according to an embodiment.

FIG. 7 schematically shows that the radiation detector may have an array of pixels, according to an embodiment.

FIG. 9A-FIG. 9C schematically show arrangements of the detectors in the image sensor, according to some embodiments.

FIG. 17 schematically shows a radiation computed tomography (Radiation CT) system comprising the system described herein, according to an embodiment.

DETAILED DESCRIPTION

Figure 1A:
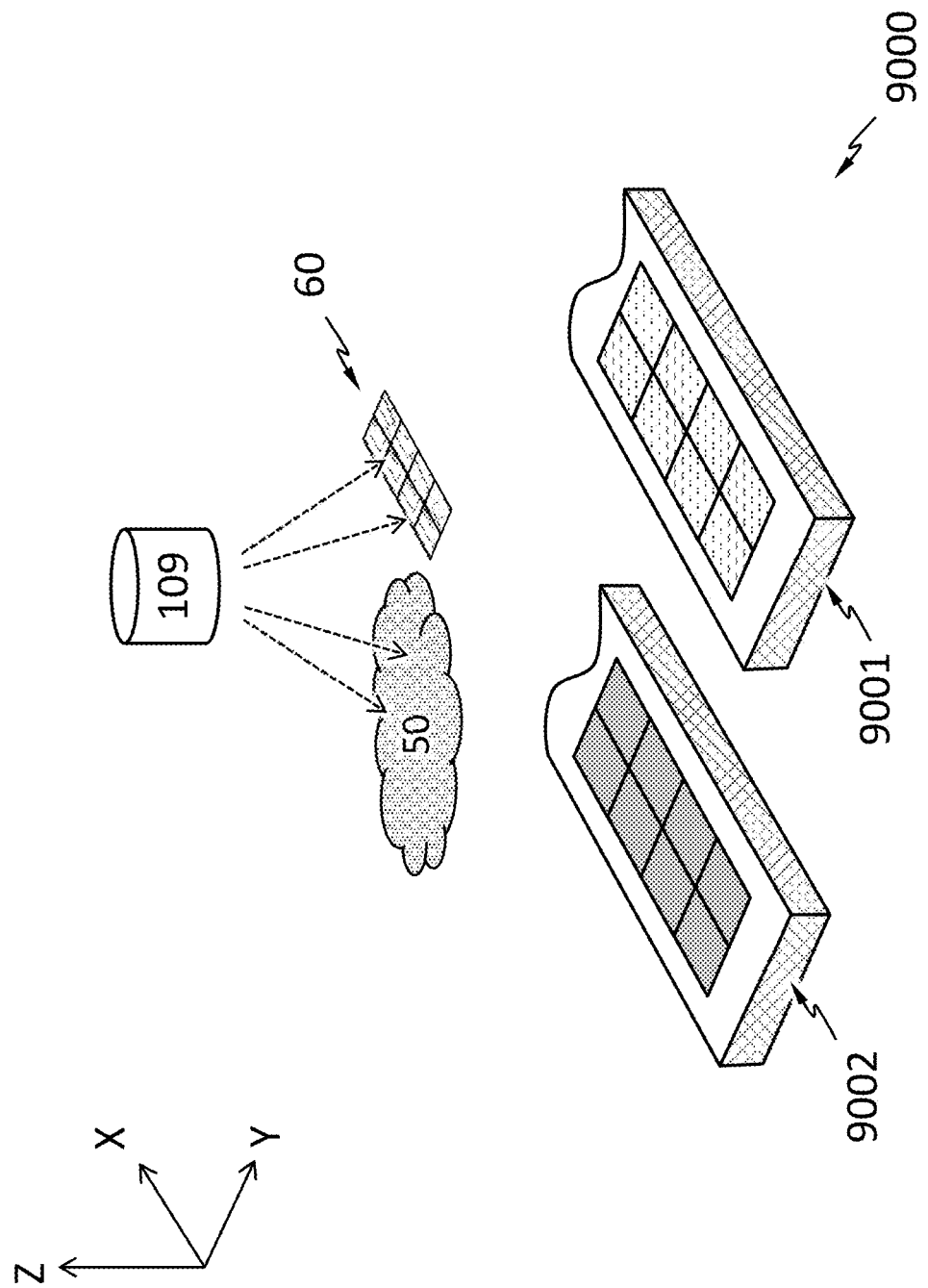
FIG. 1A schematically shows a portion of a system, according to an embodiment.

FIG. 1A schematically shows a portion of a system 9000 comprising a radiation source 109, a marker 60, a first image sensor 9001, and a second image sensor 9002, according to an embodiment. The first image sensor 9001 is configured to capture images of the marker 60, e.g., using the radiation from the radiation source 109. The second image sensor 9002 and the radiation source 109 may collectively rotate to a plurality of rotational positions relative to the scene 50. The second image sensor 9002 may move between multiple positions relative to the radiation source 109. At one of the multiple positions relative to the radiation source 109, the second image sensor 9002 may capture a set of images of portions of the scene 50 using the radiation from the radiation source 109; at another of the multiple positions relative to the radiation source 109, the second image sensor 9002 may capture another set of images of portions of the scene 50 using the radiation from the radiation source 109, e.g., respectively when the second image sensor 9002 and the radiation source 109 are at the plurality of rotational positions relative to the scene 50. The second image sensor 9002 may comprise a radiation-receiving surface configured to receive radiation, e.g., radiation that is from the radiation source 109 and may have passed through the scene 50.

Figure 1B:
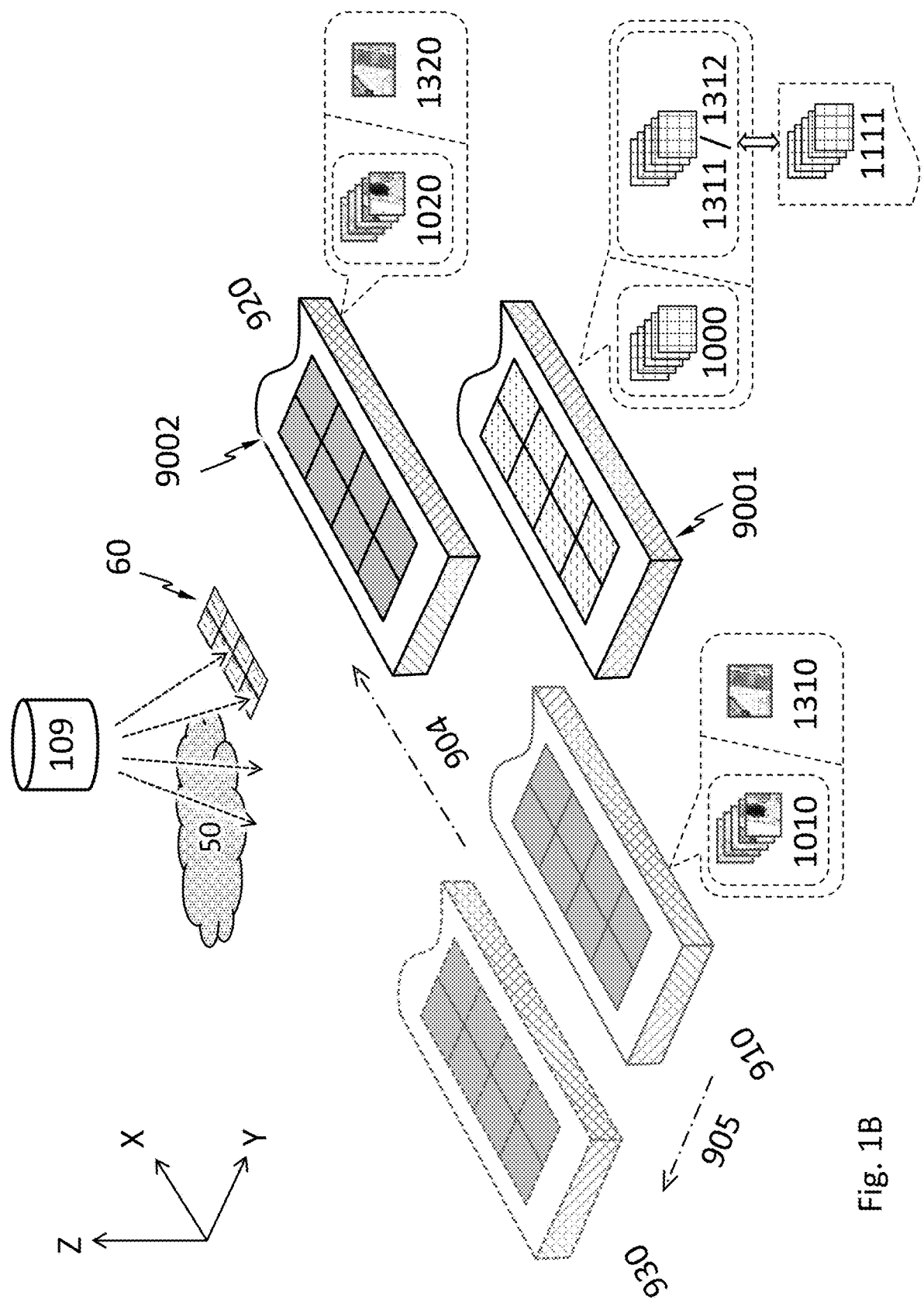
FIG. 1B and FIG. 1C each schematically show movements of the second image sensor in the system of FIG. 1A, relative to the radiation source, according to an embodiment.
Figure 1C:
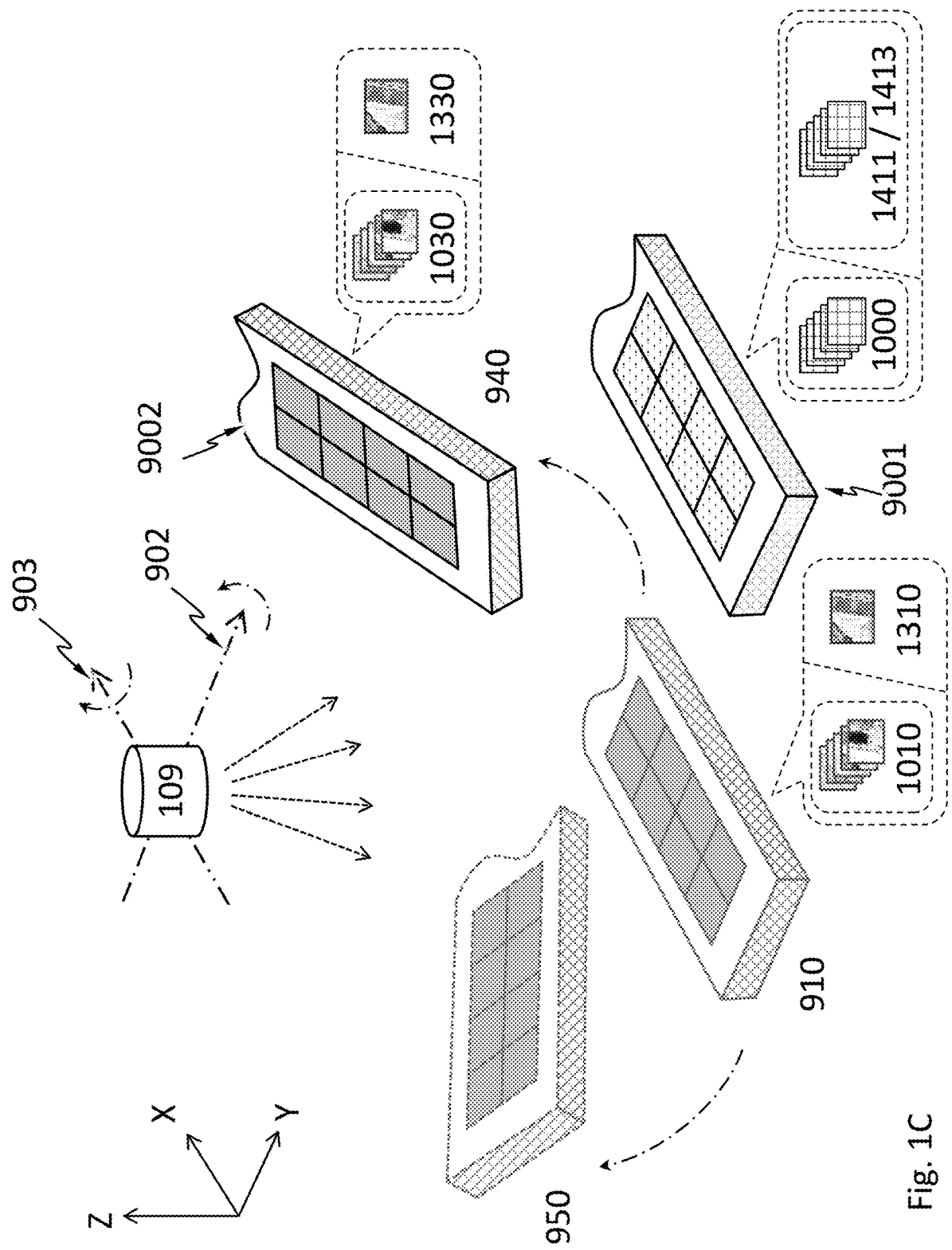

FIG. 1B and FIG. 1C each schematically show movements of the second image sensor 9002 relative to the radiation source 109, according to an embodiment. In the example shown in FIG. 1B, the second image sensor 9002 may move from a first position 910 relative to the radiation source 109 to a second position 920 relative to the radiation source 109 by translating along a first direction 904 relative to the radiation source 109. The first direction 904 may be parallel to a radiation-receiving surface of the second image sensor 9002.

FIG. 1B also shows that the second image sensor 9002 may move from the first position 910 relative to the radiation source 109 to a third position 930 relative to the radiation source 109 by translating along a second direction 905 relative to the radiation source 109. The second direction 905 is different from the first direction 904.

In the example shown in FIG. 1B, according to an embodiment, a first set 1010 of images of portions of the scene 50 are captured by the second image sensor 9002 with radiation from the radiation source 109, when the second image sensor 9002 is at the first position 910 relative to the radiation source 109. A second set 1020 of images of portions of the scene 50 are captured by the second image sensor 9002 with radiation from the radiation source 109, when the second image sensor 9002 is at the second position 920 relative to the radiation source 109. The images 1000 of marker 60 are captured by the first image sensor 9001, e.g., with radiation from the radiation source 109.

In the example shown in FIG. 1C, according to an embodiment, the second image sensor 9002 may move from the first position 910 relative to the radiation source 109 to a fourth position 940 relative to the radiation source 109 by rotating about a first axis 902 relative to the radiation source 109. The first axis 902 may be parallel to the radiation-receiving surface of the second image sensor 9002. The radiation source 109 may be on the first axis 902.

FIG. 1C also shows that the second image sensor 9002 may move from the first position 910 relative to the radiation source 109 to a fifth position 950 relative to the radiation source 109 by rotating about a second axis 903 relative to the radiation source 109. The second axis 903 is different from the first axis 902. For example, the second axis 903 may be perpendicular to the first axis 902. The radiation source 109 may be on the second axis 903.

In the example shown in FIG. 1C, according to an embodiment, a third set of images 1030 of portions of the scene 50 are captured by the second image sensor 9002 with radiation from the radiation source 109, when the second image sensor 9002 is at the fourth position 940 relative to the radiation source 109. A first set 1010 of images of portions of the scene 50 are captured by the second image sensor 9002 with radiation from the radiation source 109, when the second image sensor 9002 is at the first position 910 relative to the radiation source 109. The images 1000 of marker are captured by the first image sensor 9001 with radiation from the radiation source 109.

FIG. 2A and FIG. 2B each schematically show movement of the marker 60 or the first image sensor 9001 when the second image sensor 9002 and the radiation source 109 collectively rotate relative to the scene 50, according to an embodiment. In the example shown in FIG. 2A, the marker 60 is stationary relative to the scene 50, and a relative position of the first image sensor 9001 with respect to the radiation source 109 is fixed when the second image sensor 9002 and the radiation source 109 collectively rotate relative to the scene 50 about one or more axes, e.g., an axis 501. At least one of the one or more axes, e.g., the axis 501, may be on the second image sensor 9002. Namely, the first image sensor 9001, the second image sensor 9002 and the radiation source 109 collectively rotate relative to the scene 50 about the axis 501.

In the example shown in FIG. 2B, the first image sensor 9001 is stationary relative to the scene 50, and a relative position of the marker 60 with respect to the radiation source 109 is fixed when the second image sensor 9002 and the radiation source 109 collectively rotate relative to the scene 50 about the axis, e.g., the axis 501. At least one of the one or more axes, e.g., the axis 501, may be on the second image sensor 9002. Namely, the marker 60, the second image sensor 9002 and the radiation source 109 collectively rotate relative to the scene 50 about the axis 501.

According to one embodiment, the second image sensor 9002 and the radiation source 109 may collectively rotate about one or more axes, for example, the axis 501 in FIG. 2A and FIG. 2B. The second image sensor 9002 and the radiation source 109 may collectively rotate about other axes that are different than the axis 501. The axes, including axis 501, may be on the second image sensor 9002.

FIG. 3A and FIG. 3B each schematically shows operation of the system 9000, according to an embodiment. In the example shown in FIG. 3A, the second image sensor 9002 is at the first position 910 relative to the radiation source 109 (see FIG. 1B). According to one embodiment, the marker 60 remains stationary relative to the scene 50, while the radiation source 109, the first image sensor 9001, the second image sensor 9002 collectively rotate about the axis 501 relative to the scene 50 to a first rotational position 510. At the first rotational position 510, a first image 1001 of the marker 60 is captured by the first image sensor 9001, and an image 1011 of a portion of the scene 50, which belongs to the first set 1010 of images, is captured by the second image sensor 9002. The capturing of the first image 1001 of the marker 60 and the capturing of the image 1011 of the portion of the scene 50 may or may not be at the same time. The second image sensor 9002 may be configured to continue the collective rotation with the radiation source 109 and complete capturing the first set 1010 of images of the portion of the scene 50.

In the example shown in FIG. 3B, the second image sensor 9002 is at the second position 920 relative to the radiation source 109 (see FIG. 1B). According to one embodiment, the marker 60 remains stationary relative to the scene 50, while the radiation source 109, the first image sensor 9001, the second image sensor 9002 collectively rotate about the axis 501 relative to the scene 50 to a second rotational position 520. At the second rotational position 520, a second image 1002 of the marker 60 is captured by the first image sensor 9001, and an image 1021 of a portion of the scene 50, which belongs to the second set 1020 of images, is captured by the second image sensor 9002. The capturing of the second image 1002 of the marker 60 and the capturing of the image 1021 of the portion of the scene 50, may or may not be at the same time. The second image sensor 9002 may be configured to continue the collective rotation with the radiation source 109 and complete capturing the second set 1020 of images of the portion of the scene 50.

FIG. 4A and FIG. 4B each schematically shows operation of the system 9000, according to an embodiment. In the example shown in FIG. 4A, the second image sensor 9002 is at the first position 910 relative to the radiation source 109 (see in FIG. 1B). According to one embodiment, the first image sensor 9001 remains stationary relative to the scene 50, and the radiation source 109, the marker 60, the second image sensor 9002 collectively rotate about the axis 501 relative to the scene 50 to a first rotational position 510. At the first rotational position 510, a first image 1001 of the marker 60 is captured by the first image sensor 9001, and an image 1011 of the first portion of the scene 50, which belongs to the first set 1010 of images, is captured by the second image sensor 9002. The capturing of the first image 1001 of the marker 60 and the capturing of the image 1011 of the portion of the scene 50 may or may not be at the same time. The second image sensor 9002 may be configured to continue the collective rotation with the radiation source 109 and complete capturing the first set 1010 of images of the portion of the scene 50.

In the example shown in FIG. 4B, the second image sensor 9002 is at the second position 920 relative to the radiation source 109 (see FIG. 1B). According to one embodiment, the first image sensor 9001 remains stationary relative to the scene 50, and the radiation source 109, the marker 60, the second image sensor 9002 collectively rotate about the axis 501 relative to the scene 50 to a second rotational position 520. At the second rotational position 520, a second image 1002 of the marker 60 is captured by the first image sensor 9001, and an image 1021 of the second portion of the scene 50, which belongs to the second set 1020 of images, is captured by the second image sensor 9002. The capturing of the second image 1002 of the marker 60 and the capturing of the image 1021 of the portion of the scene 50, may or may not be at the same time. The second image sensor 9002 may be configured to continue the collective rotation with the radiation source 109 and complete capturing the second set 1020 of images of the portion of the scene 50.

According to an embodiment, the second image sensor 9002 is configured to form an image of the scene 50 by selecting an image (e.g., image 1011 in FIG. 3A or FIG. 4A) from the first set 1010 of images based on the images of the marker 60, selecting an image (e.g., image 1021 in FIG. 3B or FIG. 4A) from the second set 1020 of images based on the images of the marker 60, and stitching the two selected images together. The rotational position which the radiation source 109 is at when the image selected from the first set 1010 is captured and the rotational position which the radiation source 109 is at when the image selected from the second set 1020 is captured may be the same. According to one embodiment, selecting the images from the first set and the second set may be by comparing images of the marker 60. In the example in FIG. 3A and FIG. 3B, or in the example in FIG. 4A and FIG. 4B, if the image 1001 of the marker 60 and the image 1002 of the marker 60 are identical, rotational position 510 and rotational position 520 are the same and image 1011 and image 1021 can be respectively selected from the first set and the second set, and stitched.

In the example shown in FIG. 1B, according to an embodiment, a first image 1310 of portions of the scene 50 is captured by the second image sensor 9002 with radiation from the radiation source 109, when the second image sensor 9002 is at the first position 910 relative to the radiation source 109 and the first image sensor 9001 captures an image 1311 of the marker 60 that matches one of a set of reference images 1111. A second image 1320 of portions of the scene 50 is captured by the second image sensor 9002 with radiation from the radiation source 109, when the second image sensor 9002 is at the second position 920 relative to the radiation source 109 and the first image sensor 9001 captures an image 1312 of the marker 60 that matches one of the set of reference images 1111.

In the example shown in FIG. 1C, according to an embodiment, a third image 1330 of portions of the scene 50 is captured by the second image sensor 9002 with radiation from the radiation source 109, when the second image sensor 9002 is at the fourth position 940 relative to the radiation source 109 and the first image sensor 9001 captures an image 1413 of the marker 60 that matches one of a set of reference images 1111. A first image 1310 of portions of the scene 50 is captured by the second image sensor 9002 with radiation from the radiation source 109, when the second image sensor 9002 is at the first position 910 relative to the radiation source 109 and the first image sensor 9001 captures an image 1411 of the marker 60 that matches one of a set of reference images 1111.

According to an embodiment, the second image sensor 9002 is configured to form an image of the scene 50 by stitching the first image 1310 and the second image 1320, if the image 1311 and the image 1312 are identical. The image 1311 and the image 1312 being identical indicates that the rotational position which the radiation source 109 is at when the image 1311 is captured and the rotational position which the radiation source 109 is at when the image 1312 is captured are the same. According to an embodiment, the second image sensor 9002 is configured to form an image of the scene 50 by stitching the first image 1310 and the third image 1330, if the image 1411 and the image 1413 are identical. The image 1411 and the image 1413 being identical indicates that the rotational position which the radiation source 109 is at when the image 1411 is captured and the rotational position which the radiation source 109 is at when the image 1413 is captured are the same.

Figure 5A:
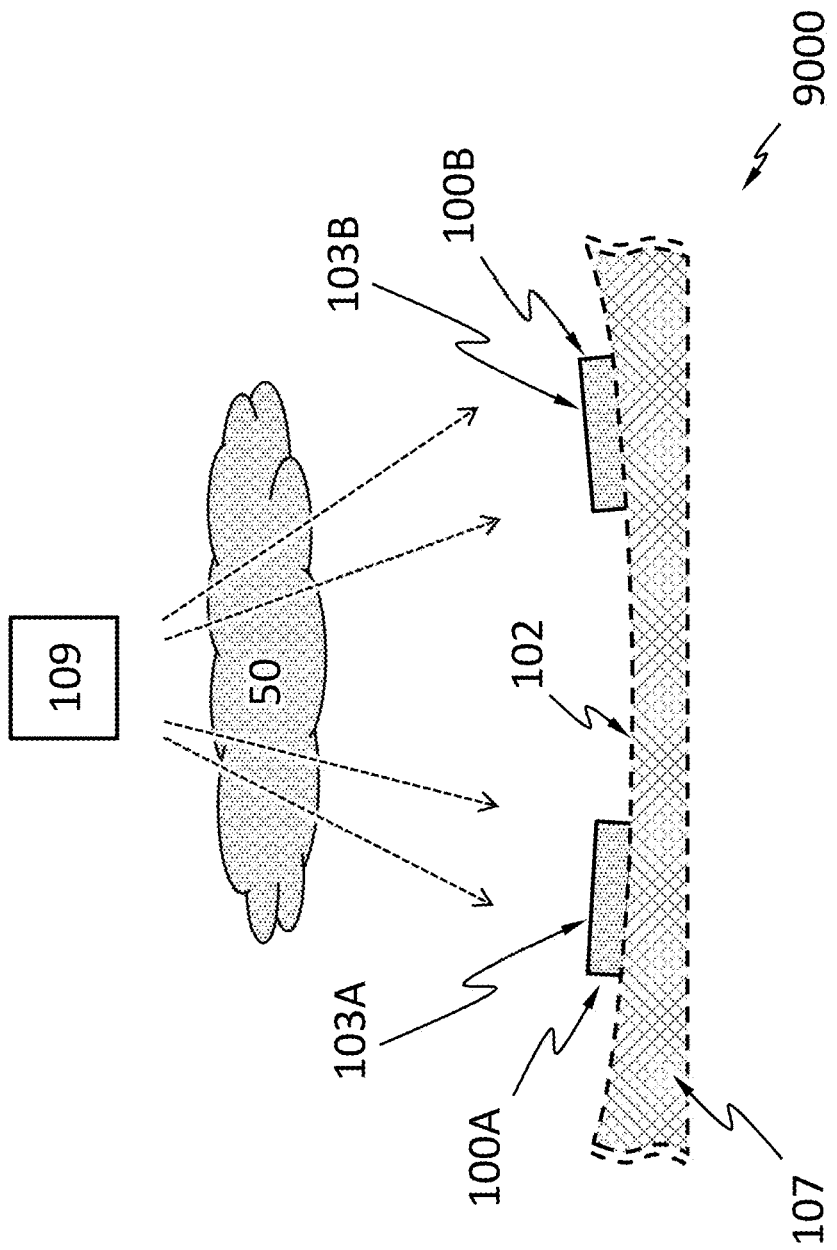
FIG. 5A schematically shows that the second image sensor may have a plurality of radiation detectors, according to an embodiment.
Figure 6A:
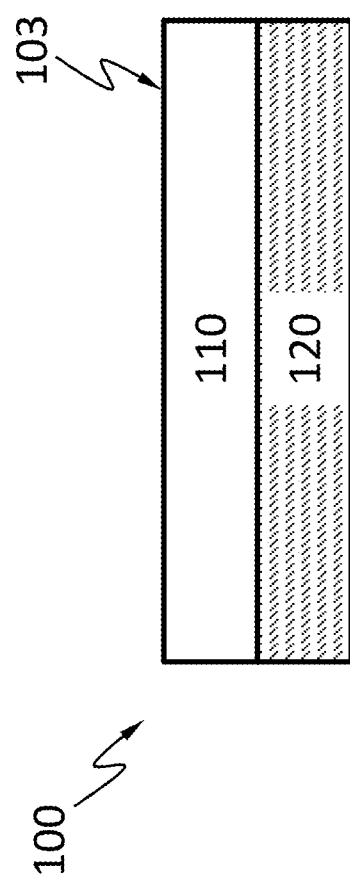
FIG. 6A schematically shows a cross-sectional view of a radiation detector, according to an embodiment.

FIG. 5A schematically shows that the second image sensor 9002 may have a plurality of radiation detectors (e.g., a first radiation detector 100A, a second radiation detector 100B). The second image sensor 9002 may have a support 107 with a curved surface 102. The plurality of radiation detectors may be arranged on the support 107, for example, on the curved surface 102, as shown in the example of FIG. 6A. The first radiation detector 100A may have a first planar surface 103A configured to receive radiation from the radiation source 109. A second radiation detector 100B may have a second planar surface 103B configured to receive the radiation from the radiation source 109. The first planar surface 103A of the first radiation detector 100A and the second planar surface 103B of the second radiation detector 100B may be not parallel. The radiation from the radiation source 109 may have passed through the scene 50 (e.g., a portion of a human body) before reaching the first radiation detector 100A or the second radiation detector 100B.

Figure 5B:
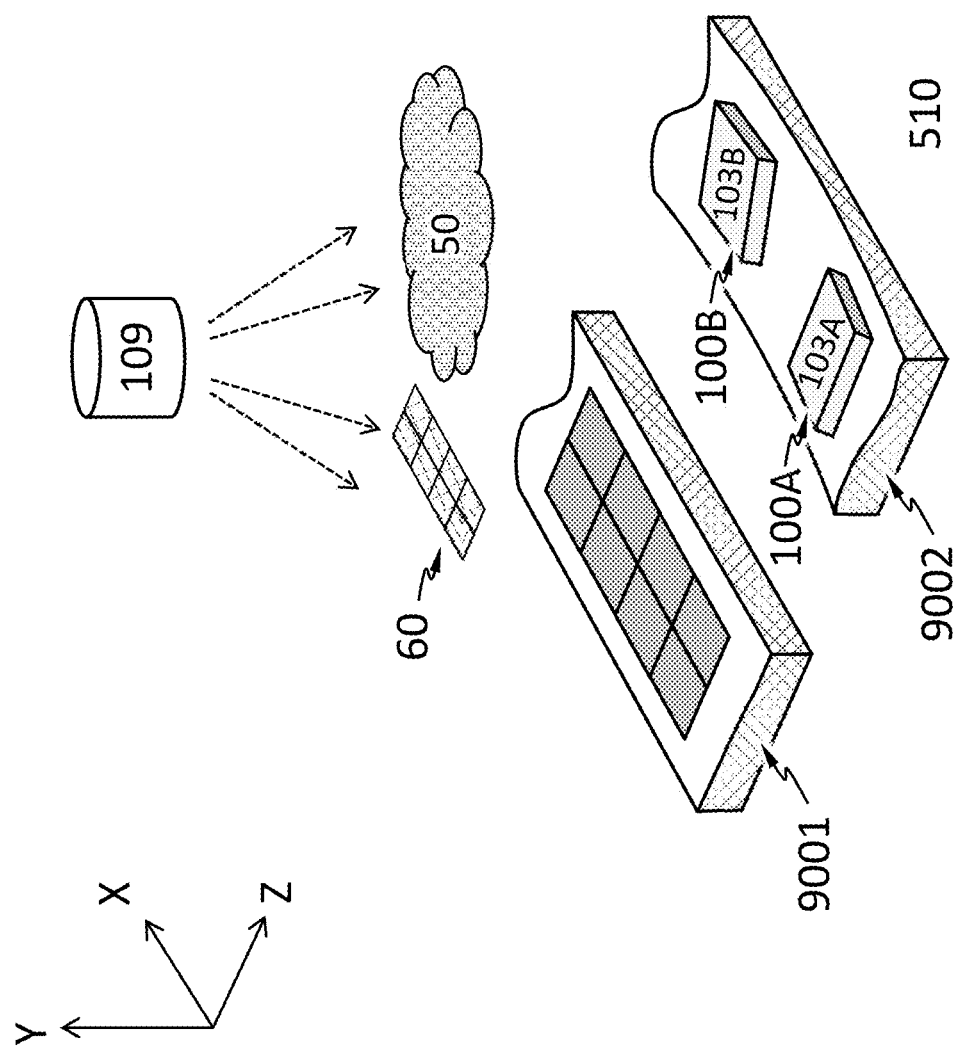
FIG. 5B schematically shows an example of a perspective view of the first image sensor and the second image sensor, with respect to the scene, the marker and the radiation source.

FIG. 5B schematically shows an example of a perspective view of the first image sensor 9001 and the second image sensor 9002 depicted in FIG. 5A, with respect to the scene 50, the marker 60 and the radiation source 109.

A relative position of the first radiation detector 100A with respect to the second radiation detector 100B may remain unchanged when the second image sensor 9002 moves relative to the radiation source 109 and when the second image sensor 9002 and the radiation source 109 collectively rotate relative to the scene 50. The first radiation detector 100A and the second radiation detector 100B remain stationary relative to the second image sensor 9002. Therefore, the first radiation detector 100A and the second radiation detector 100B may move relative to the radiation source 109 with the second image sensor 9002 by translating along the first direction 904 or the second direction 905 relative to the radiation source 109 or by rotating about the first axis 902 or the second axis 903 relative to the radiation source 109. The first direction 904 or the second direction 905 may be parallel to both, either or neither of the first planar surface 103A and the second planar surface 103B. For example, the first direction 904 may be parallel to the first planar surface 103A, but not parallel to the second planar surface 103B.

FIG. 6A schematically shows a cross-sectional view of a radiation detector 100, according to an embodiment. The radiation detector 100 may be used in the image sensors in the system 9000, for example as the first radiation detector 100A or the second radiation detector 1006. The radiation detector 100 may include a radiation absorption layer 110 and an electronics layer 120 (e.g., an ASIC) for processing or analyzing electrical signals incident radiation generates in the radiation absorption layer 110. In an embodiment, the radiation detector 100 does not comprise a scintillator. The radiation absorption layer 110 may include a semiconductor material such as, silicon, germanium, GaAs, CdTe, CdZnTe, or a combination thereof. The semiconductor may have a high mass attenuation coefficient for the radiation energy of interest. The surface 103 of the radiation absorption layer 110 distal from the electronics layer 120 is configured to receive radiation.

Figure 6B:
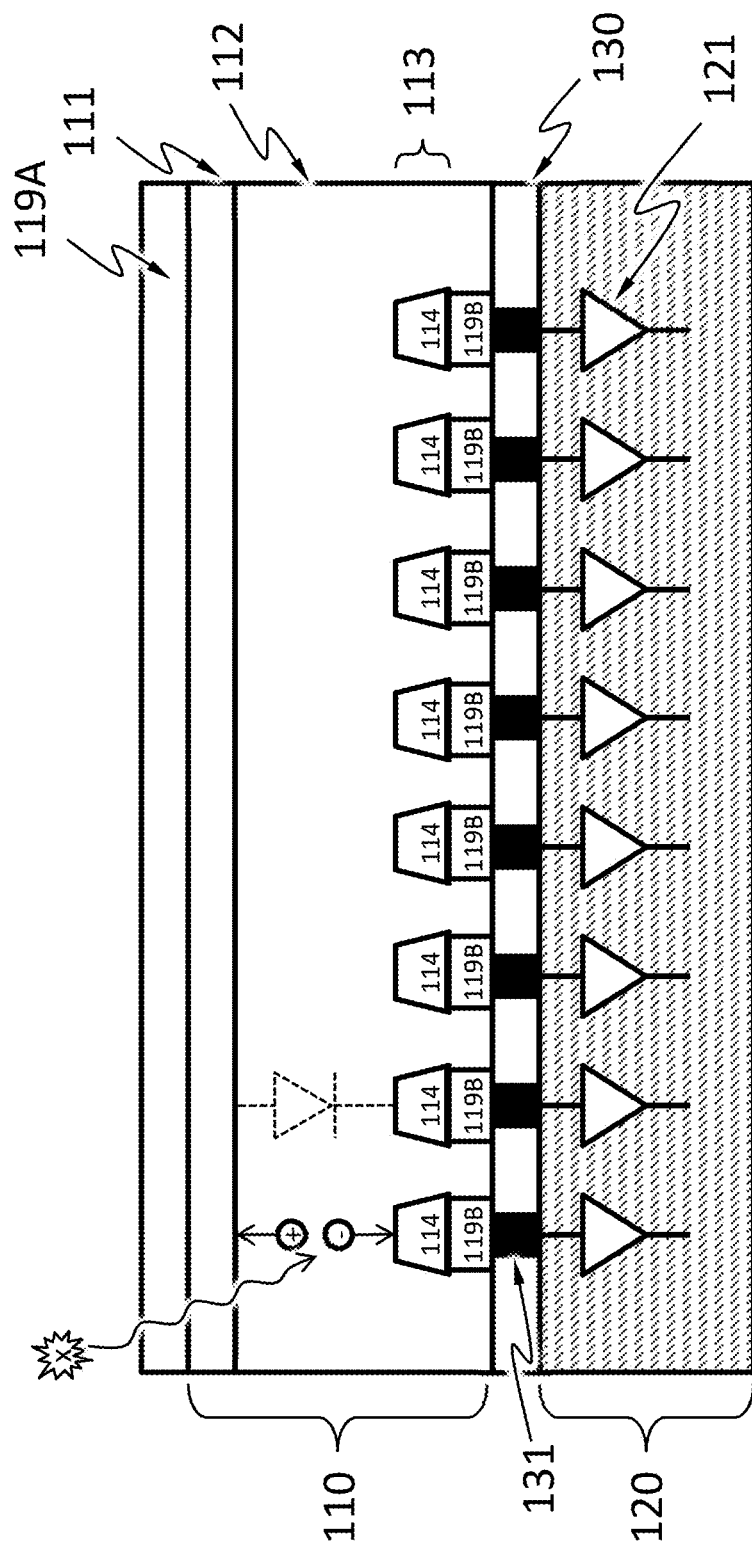
FIG. 6B schematically shows a detailed cross-sectional view of the detector, according to an embodiment.

As shown in a detailed cross-sectional view of the radiation detector 100 in FIG. 6B, according to an embodiment, the radiation absorption layer 110 may include one or more diodes (e.g., p-i-n or p-n) formed by a first doped region 111, one or more discrete regions 114 of a second doped region 113. The second doped region 113 may be separated from the first doped region 111 by an optional the intrinsic region 112. The discrete regions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example in FIG. 6B, each of the discrete regions 114 of the second doped region 113 forms a diode with the first doped region 111 and the optional intrinsic region 112. Namely, in the example in FIG. 6B, the radiation absorption layer 110 has a plurality of diodes having the first doped region 111 as a shared electrode. The first doped region 111 may also have discrete portions.

When a radiation particle hits the radiation absorption layer 110 including diodes, the radiation particle may be absorbed and generate one or more charge carriers by a number of mechanisms. A radiation particle may generate 10 to 100000 charge carriers. The charge carriers may drift to the electrodes of one of the diodes under an electric field. The field may be an external electric field. The electric contact 119B may include discrete portions each of which is in electrical contact with the discrete regions 114. In an embodiment, the charge carriers may drift in directions such that the charge carriers generated by a single radiation particle are not substantially shared by two different discrete regions 114 ("not substantially shared" here means less than 2%, less than 0.5%, less than 0.1%, or less than 0.01% of these charge carriers flow to a different one of the discrete regions 114 than the rest of the charge carriers). Charge carriers generated by a radiation particle incident around the footprint of one of these discrete regions 114 are not substantially shared with another of these discrete regions 114. A pixel 150 associated with a discrete region 114 may be an area around the discrete region 114 in which substantially all (more than 98%, more than 99.5%, more than 99.9%, or more than 99.99% of) charge carriers generated by a radiation particle incident therein at an angle of incidence of 0° flow to the discrete region 114. Namely, less than 2%, less than 1%, less than 0.1%, or less than 0.01% of these charge carriers flow beyond the pixel.

Figure 6C:
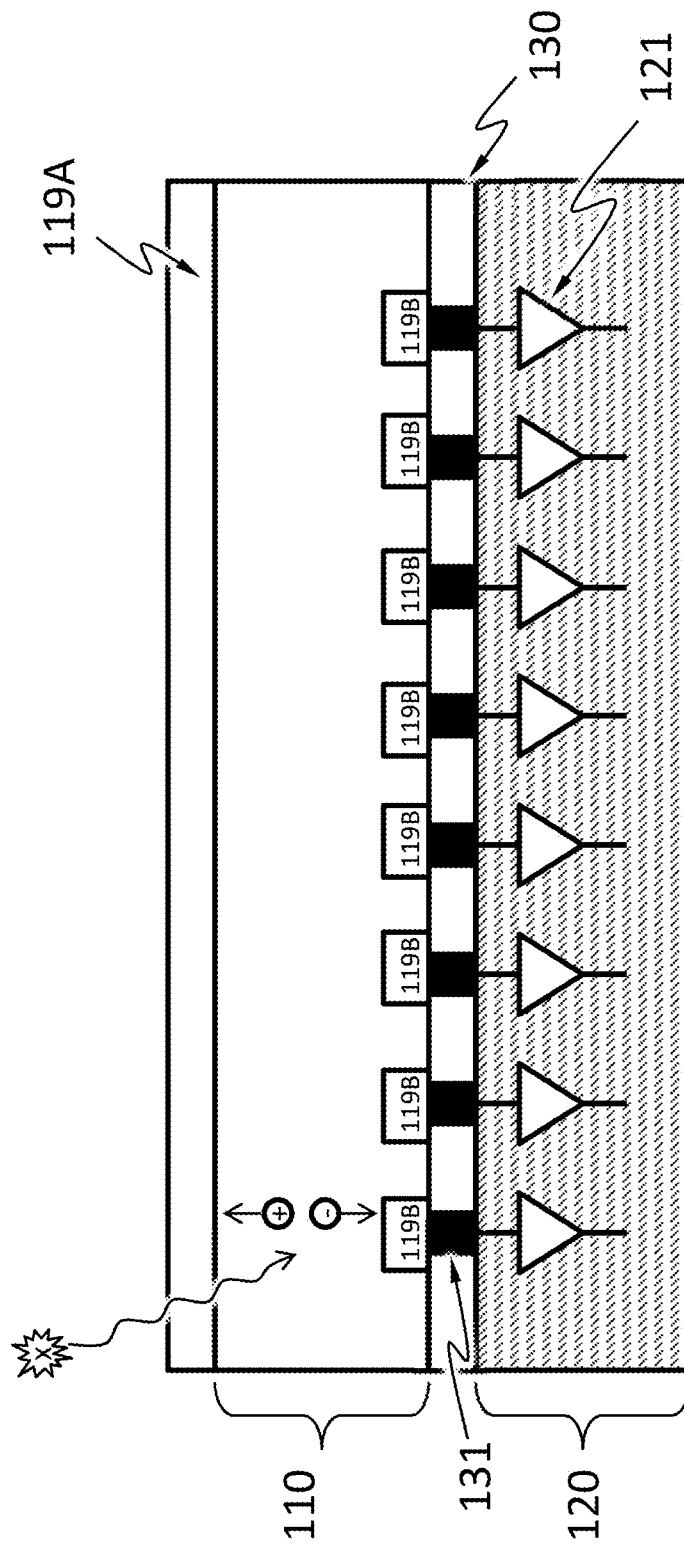
FIG. 6C schematically shows an alternative detailed cross-sectional view of the detector, according to an embodiment.

As shown in an alternative detailed cross-sectional view of the radiation detector 100 in FIG. 6C, according to an embodiment, the radiation absorption layer 110 may include a resistor of a semiconductor material such as, silicon, germanium, GaAs, CdTe, CdZnTe, or a combination thereof, but does not include a diode. The semiconductor may have a high mass attenuation coefficient for the radiation energy of interest.

When a radiation particle hits the radiation absorption layer 110 including a resistor but not diodes, it may be absorbed and generate one or more charge carriers by a number of mechanisms. A radiation particle may generate 10 to 100000 charge carriers. The charge carriers may drift to the electric contacts 119A and 119B under an electric field. The field may be an external electric field. The electric contact 119B includes discrete portions. In an embodiment, the charge carriers may drift in directions such that the charge carriers generated by a single radiation particle are not substantially shared by two different discrete portions of the electric contact 119B ("not substantially shared" here means less than 2%, less than 0.5%, less than 0.1%, or less than 0.01% of these charge carriers flow to a different one of the discrete portions than the rest of the charge carriers). Charge carriers generated by a radiation particle incident around the footprint of one of these discrete portions of the electric contact 119B are not substantially shared with another of these discrete portions of the electric contact 119B. A pixel 150 associated with a discrete portion of the electric contact 119B may be an area around the discrete portion in which substantially all (more than 98%, more than 99.5%, more than 99.9% or more than 99.99% of) charge carriers generated by a radiation particle incident at an angle of incidence of 0° therein flow to the discrete portion of the electric contact 119B. Namely, less than 2%, less than 0.5%, less than 0.1%, or less than 0.01% of these charge carriers flow beyond the pixel associated with the one discrete portion of the electric contact 119B.

The electronics layer 120 may include an electronic system 121 suitable for processing or interpreting signals generated by radiation particles incident on the radiation absorption layer 110. The electronic system 121 may include an analog circuitry such as a filter network, amplifiers, integrators, and comparators, or a digital circuitry such as a microprocessor, and memory. The electronic system 121 may include components shared by the pixels or components dedicated to a single pixel. For example, the electronic system 121 may include an amplifier dedicated to each pixel and a microprocessor shared among all the pixels. The electronic system 121 may be electrically connected to the pixels by vias 131. Space among the vias may be filled with a filler material 130, which may increase the mechanical stability of the connection of the electronics layer 120 to the radiation absorption layer 110. Other bonding techniques are possible to connect the electronic system 121 to the pixels without using vias.

FIG. 7 schematically shows that the radiation detector 100 may have an array of pixels 150. The array may be a rectangular array, a honeycomb array, a hexagonal array or any other suitable array. Each pixel 150 may be configured to detect a radiation particle incident thereon, measure the energy of the radiation particle, or both. For example, each pixel 150 may be configured to count numbers of radiation particles incident thereon whose energy falls in a plurality of bins, within a period of time. All the pixels 150 may be configured to count the numbers of radiation particles incident thereon within a plurality of bins of energy within the same period of time. Each pixel 150 may have its own analog-to-digital converter (ADC) configured to digitize an analog signal representing the energy of an incident radiation particle into a digital signal. The ADC may have a resolution of 10 bits or higher. Each pixel 150 may be configured to measure its dark current, such as before or concurrently with each radiation particle incident thereon. Each pixel 150 may be configured to deduct the contribution of the dark current from the energy of the radiation particle incident thereon. The pixels 150 may be configured to operate in parallel. For example, when one pixel 150 measures an incident radiation particle, another pixel 150 may be waiting for another radiation particle to arrive. The pixels 150 may be but do not have to be individually addressable.

Figure 8:
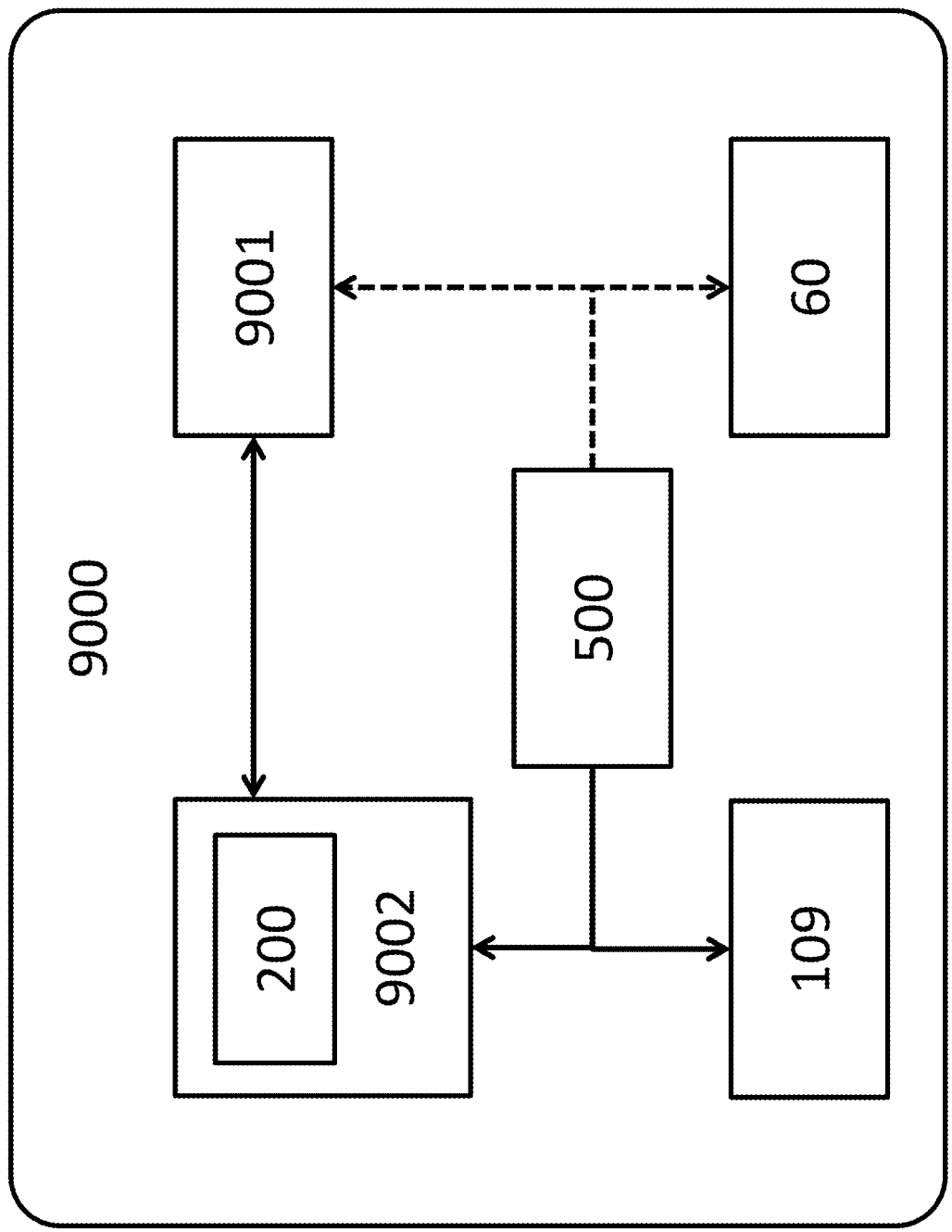
FIG. 8 schematically shows a functional block diagram of the system, according to an embodiment.

According to an embodiment, the second image sensor 9002 can move to multiple positions, relative to the radiation source 109. The second image sensor 9002 may use the radiation detectors 100 and with the radiation from the radiation source 109 to capture images of multiple portions of the scene 50 respectively at the multiple positions. The second image sensor 9002 can compare the images of marker captured by the first image sensor 9001 and stitch the images of portions of the scene 50 captured by the second image sensor to form an image of the entire scene 50. As shown in FIG. 8, according to an embodiment, the system 9000 may include an actuator 500 configured to move the second image sensor 9002 to the multiple positions. The second image sensor 9002 may include a processor 200 that compares images of marker to determine the rotational positions of the second image sensor 9002. The processor 200 may be used to stitch the images of portions of the scene 50. The rotational positions of the second image sensor 9002 and the radiation source 109 may be controlled by the actuator 500. The rotational positions of the first image sensor 9001 and the marker 60 may be optionally controlled by the actuator 500.

The radiation detectors 100 may be arranged in a variety of ways in the second image sensor 9002. FIG. 9A schematically shows one arrangement, according to an embodiment, where the radiation detectors 100 are arranged in staggered rows. For example, radiation detectors 100A and 100B are in the same row, aligned in the Y direction, and uniform in size; radiation detectors 100C and 100D are in the same row, aligned in the Y direction, and uniform in size. Radiation detectors 100A and 100B are staggered in the X direction with respect to radiation detectors 100C and 100D. According to an embodiment, a distance X2 between two neighboring radiation detectors 100A and 100B in the same row is greater than a width X1 (i.e., dimension in the X direction, which is the extending direction of the row) of one radiation detector in the same row and is less than twice the width X1. Radiation detectors 100A and 100E are in a same column, aligned in the X direction, and uniform in size; a distance Y2 between two neighboring radiation detectors 100A and 100E in the same column is less than a width Y1 (i.e., dimension in the Y direction) of one radiation detector in the same column. An image of the scene using this arrangement may be obtained from stitching three images of portions of the scene captured at three positions spaced apart in the X direction.

FIG. 10B schematically shows another arrangement, according to an embodiment, where the radiation detectors 100 are arranged in a rectangular grid. For example, the radiation detectors 100 may include radiation detectors 100A, 100B, 100E and 100F as arranged exactly in FIG. 10A, without radiation detectors 100C, 100D, 100G, or 100H in FIG. 9A. This arrangement allows imaging of the scene by taking images of portions of the scene at six positions. For example, three positions spaced apart in the X direction and another three positions spaced apart in the X direction and spaced apart in the Y direction from the first three positions.

Other arrangements may also be possible. For example, in FIG. 9C, the radiation detectors 100 may span the whole width of the image sensor 9001 or 9002 in the X-direction, with a distance Y2 between two neighboring radiation detectors 100 being less than a width of one radiation detector Y1. Assuming the width of the detectors in the X direction is greater than the width of the scene in the X direction, the image of the scene may be stitched from two images of portions of the scene captured at two positions spaced apart in the Y direction.

Figure 10:
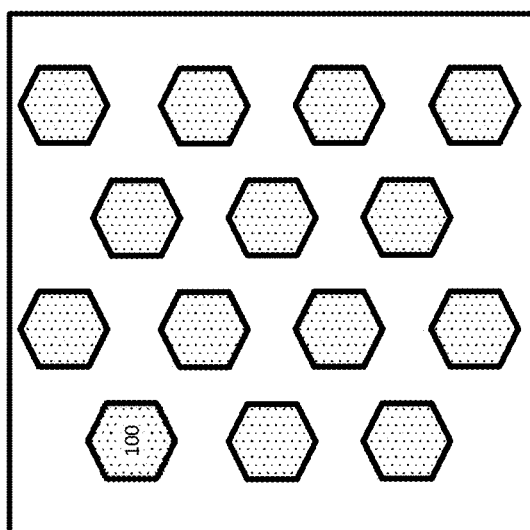
FIG. 10 schematically shows an image sensor with plurality of detectors that are hexagonal in shape, according to an embodiment.

The radiation detectors 100 described above may be provided with any suitable size and shapes. According to an embodiment (e.g., in FIG. 9A, FIG. 9B, and FIG. 9C), at least some of the radiation detectors are rectangular in shape. According to an embodiment, as shown in FIG. 10, at least some of the radiation detectors are hexagonal in shape.

Figure 11:
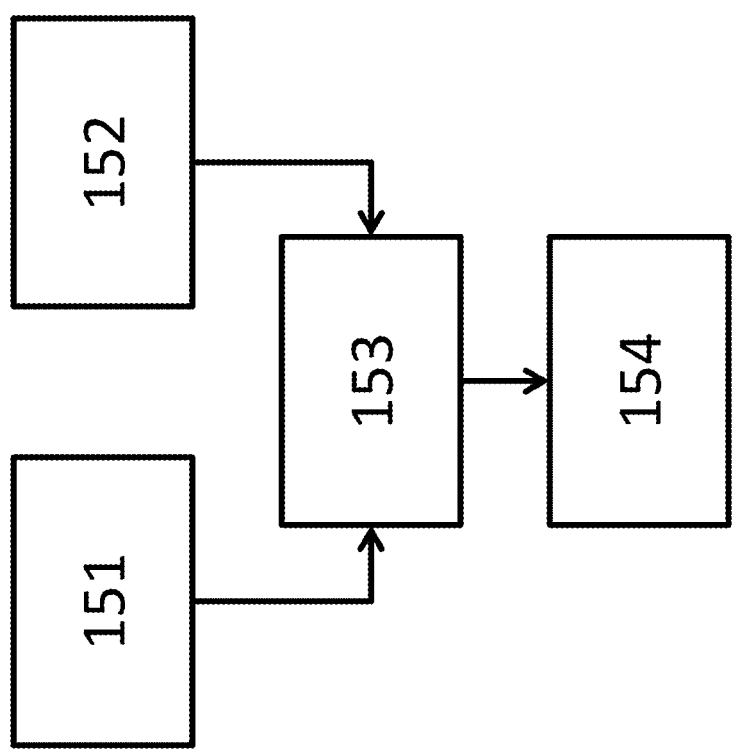
FIG. 11 and FIG. 12 each schematically show a flowchart for a method, according to an embodiment.

FIG. 11 schematically shows a flowchart for a method, according to an embodiment. In procedure 151, an image of first portions of the scene 50 is captured with radiation from the radiation source 109 (e.g., by the second image sensor 9002 when it is at the first position 910 relative to the radiation source 109) and a first image of the marker 60 is captured (e.g., by the first image sensor 9001), when the radiation source 109 is at the first rotational position 510 relative to the scene 50. The first image of the marker 60 is not necessarily captured at the same time as the first of first portions of the scene 50. In procedure 152, an image of second portions of the scene 50 is captured (e.g., by the second image sensor 9002 when it is at the second position 920 relative to the radiation source 109) with radiation from the radiation source 109 and a second image of the marker 60 is captured (e.g., by the first image sensor 9001), when the radiation source 109 is at the second rotational position 520 relative to the scene 50. The second image of the marker 60 is not necessarily captured at the same time as the image of the second portions of the scene 50. In procedure 153, whether the first rotational position 510 and the second rotational position 520 are the same is determined based on the first image of the marker and the second image of the marker. In an example, whether the first rotational position 510 and the second rotational position 520 are the same involves determining the first rotation position 510 based on the first image of the marker and determining the second rotational position 520 based on the second image of the marker. In an example, whether the first rotational position 510 and the second rotational position 520 are the same involves determining whether the first image of the marker and the second image of the marker are identical. In procedure 154, an image of the scene 50 is formed by stitching the image of the first portions and the image of the second portions, upon determining that the first rotational position 510 and the second rotational position 520 are the same.

Figure 12:
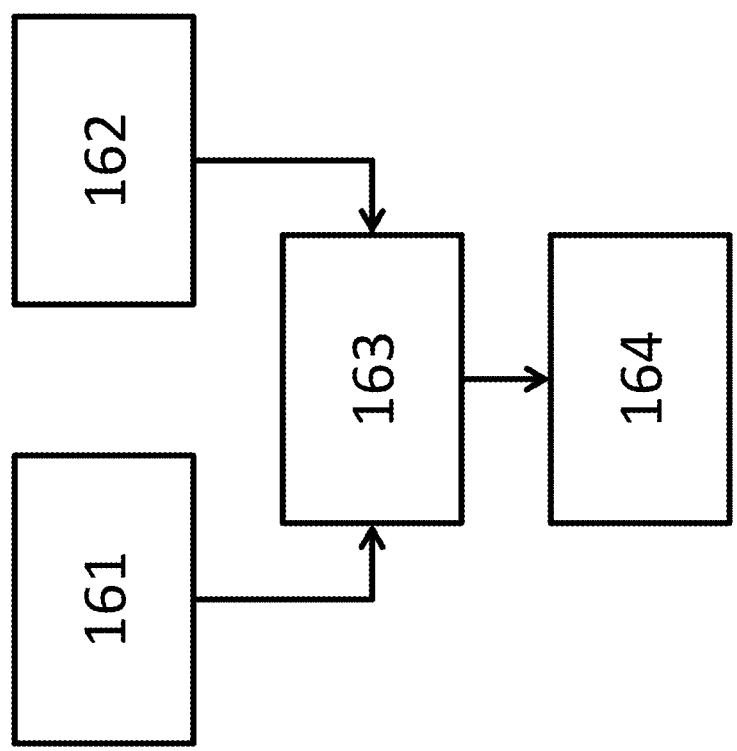

FIG. 12 schematically shows a flowchart for a method, according to an embodiment. In procedure 161, an image of first portions of the scene 50 is captured with radiation from the radiation source 109 (e.g., by the second image sensor 9002 at the first position 910 relative to the radiation source 109), when a first image of the marker 60 is captured and matches one of a set of reference images. The first image of the marker 60 is not necessarily captured at the same time as the image of first portions of the scene 50. In procedure 162, an image of second portions of the scene 50 is captured (e.g., by the second image sensor 9002 when it is at the second position 920 relative to the radiation source 109) with radiation from the radiation source 109 by the second image sensor 9002, when a second image of the marker 60 is captured matches one of a set of reference images. The second image of the marker 60 is not necessarily captured at the same time as the image of second portion of the scene 50. In procedure 163, whether the first image of the marker and the second image of the marker are identical is determined. For example, the rotational position which the radiation source 109 is at when the first image of the marker is captured and the rotational position which the radiation source 109 is at when the second image of the marker is captured are the same. When the first image of the marker and the second image of the marker are identical, the first rotational position and the second rotational position are the same. In procedure 164, an image of the scene 50 is formed by stitching the image of the first portions and the image of the second portions, upon determining that the first image of the marker and the second image of the marker 60 are identical.

The system 9000 described above may be used in various systems such as those provided below.

Figure 13:
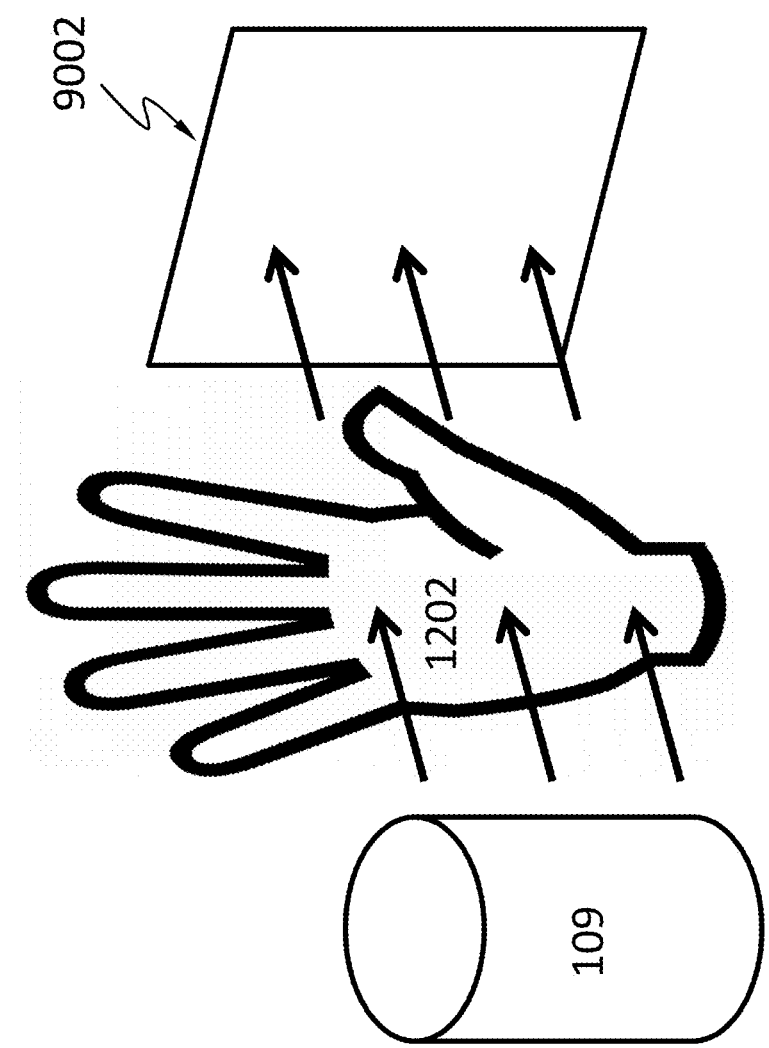
FIG. 13 schematically shows a system comprising the system described herein, suitable for medical imaging such as chest radiation radiography, abdominal radiation radiography, etc., according to an embodiment FIG. 14 schematically shows a system comprising the system described herein suitable for dental radiation radiography, according to an embodiment.

FIG. 13 schematically shows that the system 9000 as described above may be used for medical imaging such as chest radiation radiography, abdominal radiation radiography, etc. Radiation emitted from the radiation source 109 penetrates an object 1202 (e.g., a human body part such as chest, limb, abdomen), is attenuated by different degrees by the internal structures of the object 1202 (e.g., bones, muscle, fat and organs, etc.), and is projected to the second image sensors 9002.

Figure 14:
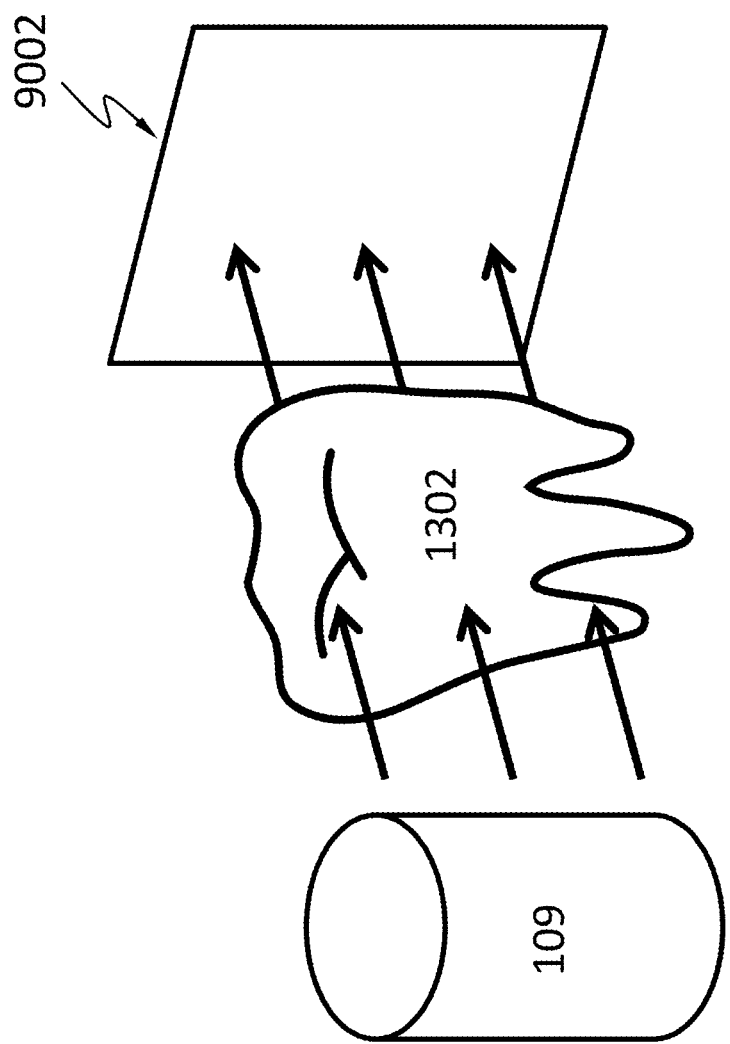

FIG. 14 schematically shows that the system 9000 as described above may be used for medical imaging such as dental radiation radiography. Radiation emitted from the radiation source 109 penetrates an object 1302 that is part of a mammal (e.g., human) mouth. The object 1302 may include a maxilla bone, a palate bone, a tooth, the mandible, or the tongue. The radiation is attenuated by different degrees by the different structures of the object 1302 and is projected to the second image sensors 9002. Teeth absorb radiation more than dental caries, infections, periodontal ligament. The dosage of radiation received by a dental patient is typically small (around 0.150 mSv for a full mouth series).

Figure 15:
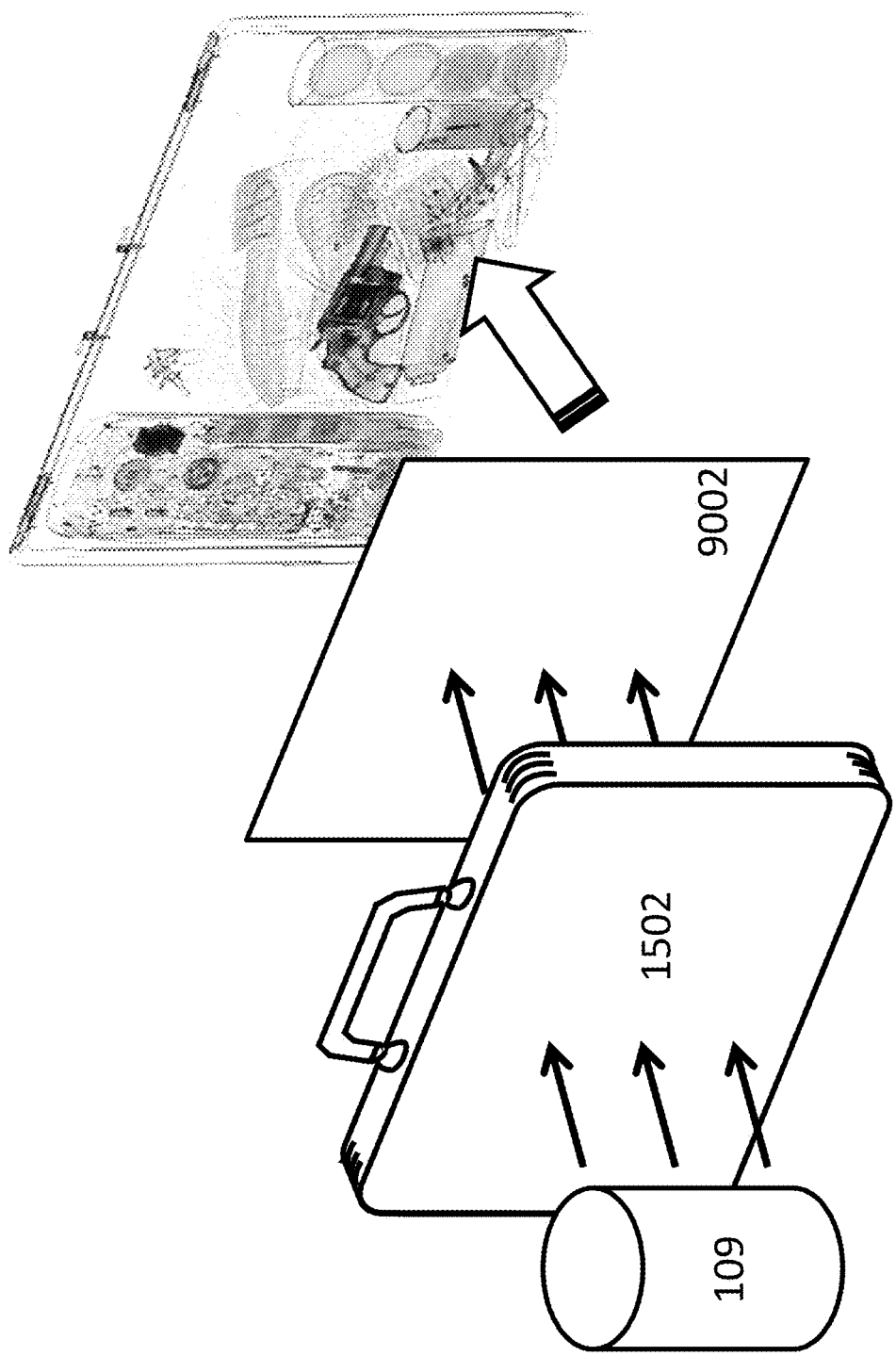
FIG. 15 schematically shows a cargo scanning or non-intrusive inspection (NII) system comprising the image sensor described herein, according to an embodiment.

FIG. 15 schematically shows that the system 9000 as described above may be used for cargo scanning or non-intrusive inspection (NII), e.g., at public transportation facilities. Radiation emitted from the radiation source 109 may penetrate a piece of luggage 1502, be differently attenuated by the contents of the luggage, and projected to the second image sensor 9002. The system may reveal contents of luggage and identify items forbidden on public transportation, such as firearms, narcotics, edged weapons, flammables.

Figure 16:
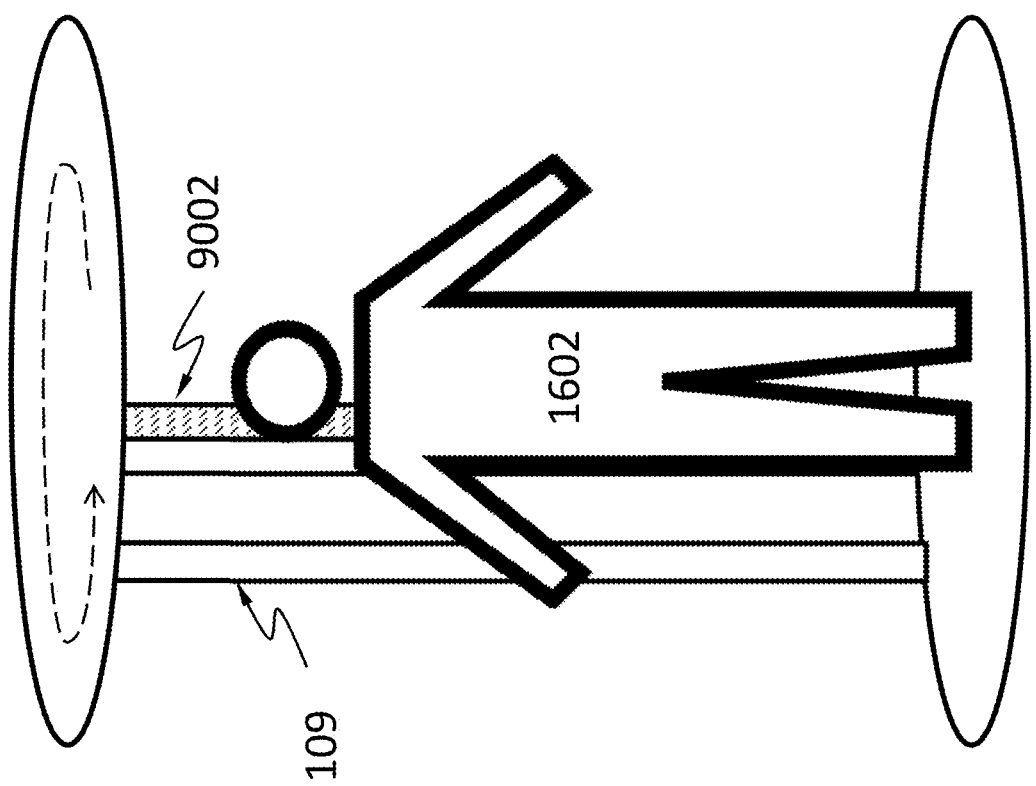
FIG. 16 schematically shows a full-body scanner system comprising the system described herein, according to an embodiment.

FIG. 16 schematically shows that the system 9000 as described above may be used as a full-body scanner for detecting metal or non-metal objects on a person's body for security screening purposes, without physically removing clothes or making physical contact. Radiation emitted from the radiation source 109 may backscatter from a human 1602 being screened and objects thereon and be projected to the second image sensor 9002. The objects and the human body may backscatter radiation differently. The radiation source 109 may be configured to scan the human in a linear or rotational direction.

FIG. 17 schematically shows that the system 9000 as described above may be used for a radiation computed tomography (Radiation CT). Radiation CT uses computer-processed radiations to produce tomographic images (virtual "slices") of specific areas of a scanned object. The tomographic images may be used for diagnostic and therapeutic purposes in various medical disciplines, or for flaw detection, failure analysis, metrology, assembly analysis and reverse engineering. The radiation source 109 may be configured to rotate synchronously along one or more circular or spiral paths.

The system 9000 described here may have other applications such as in a radiation telescope, radiation mammography, industrial radiation defect detection, radiation microscopy or microradiography, radiation casting inspection, radiation non-destructive testing, radiation weld inspection, radiation digital subtraction angiography, etc. It may be suitable to use the system 9000 in place of a photographic plate, a photographic film, a PSP plate, a radiation image intensifier, a scintillator, or another semiconductor radiation detector.

Figure 18A:
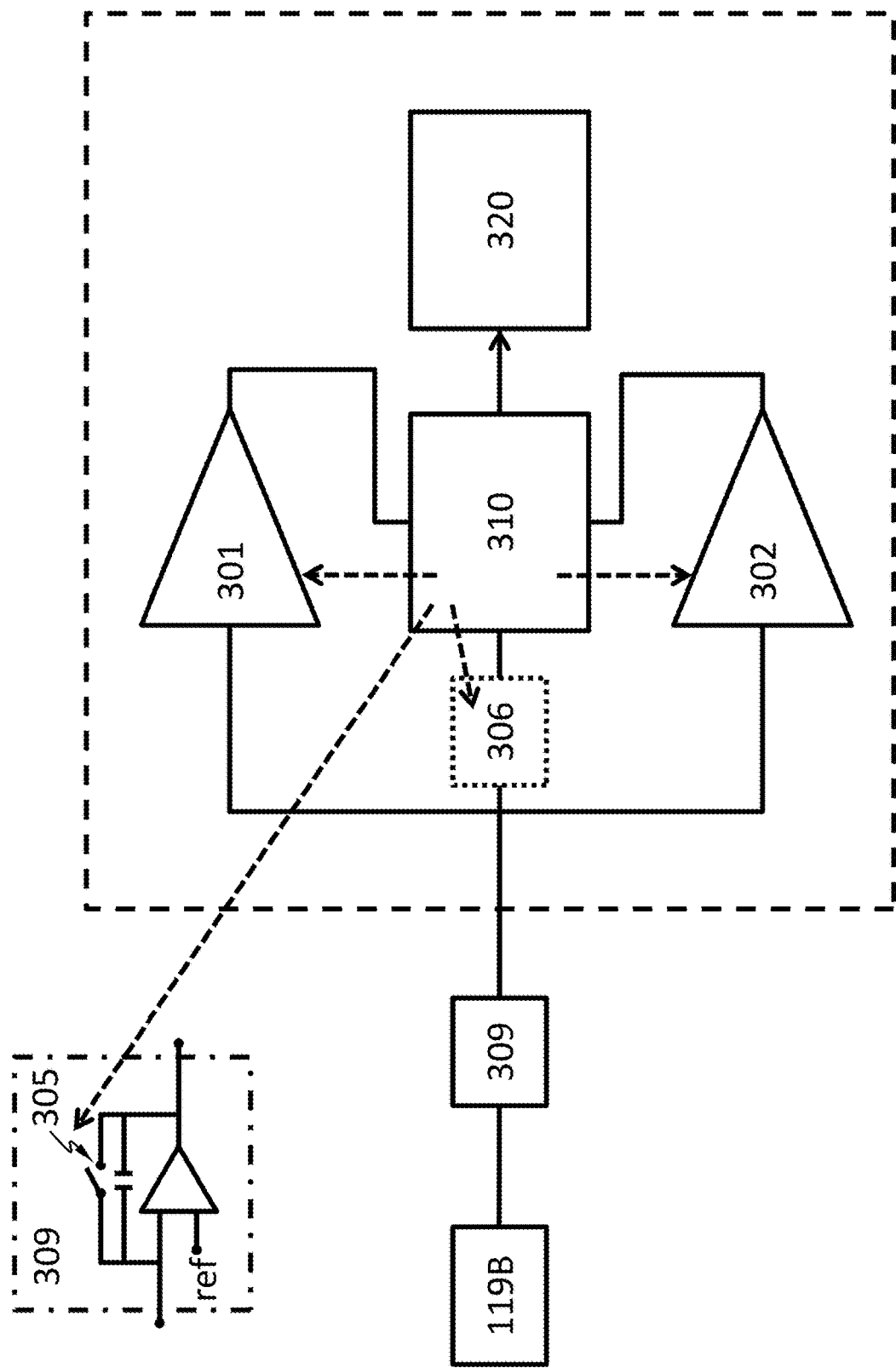
FIG. 18A and FIG. 18B each show a component diagram of an electronic system of the radiation detector in FIG. 6A, FIG. 6B and FIG. 6C, according to an embodiment.
Figure 18B:
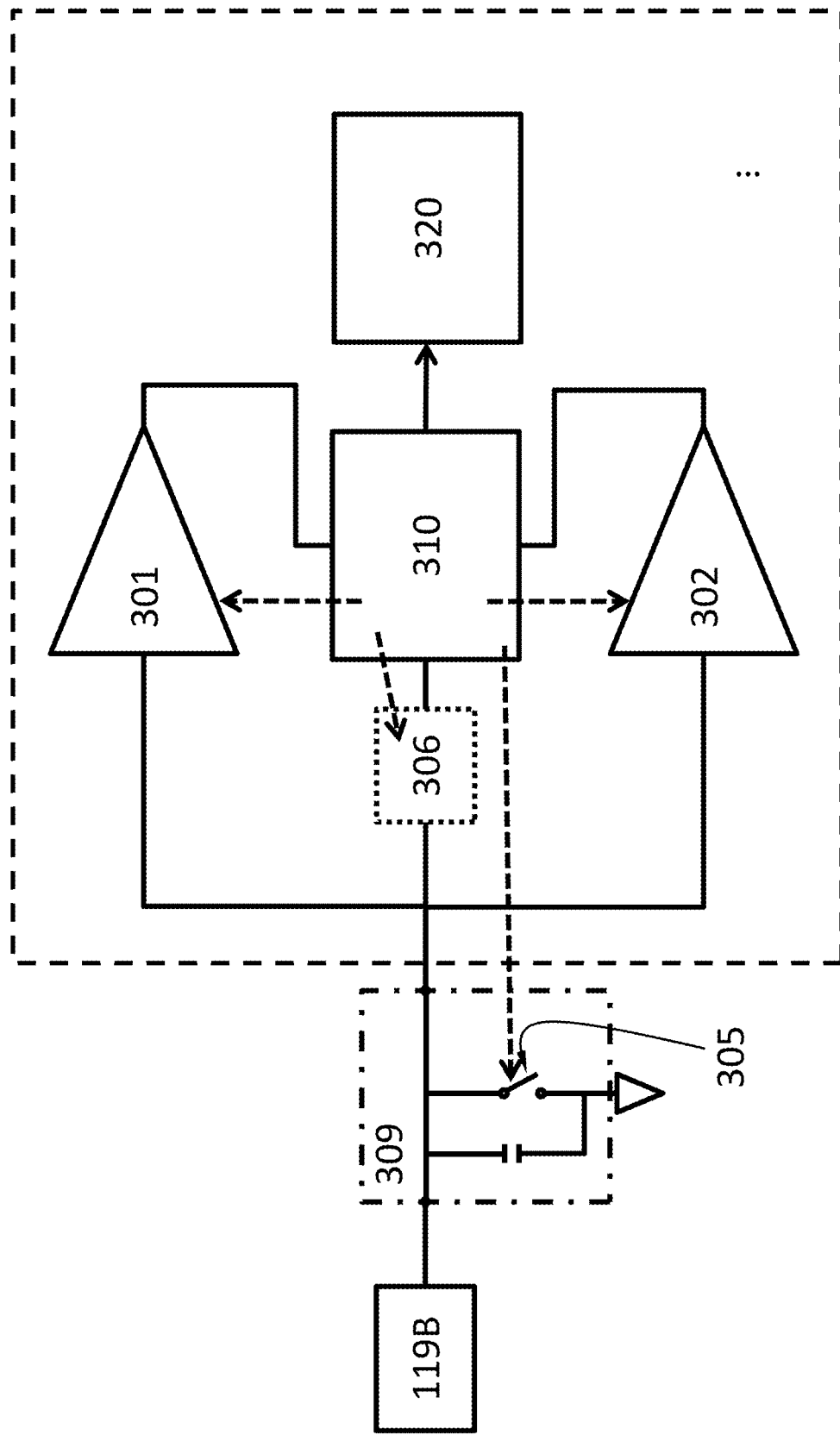

FIG. 18A and FIG. 18B each show a component diagram of the electronic system 121, according to an embodiment. The electronic system 121 may include a first voltage comparator 301, a second voltage comparator 302, a counter 320, a switch 305, an optional voltmeter 306 and a controller 310.

The first voltage comparator 301 is configured to compare the voltage of at least one of the electric contacts 119B to a first threshold. The first voltage comparator 301 may be configured to monitor the voltage directly, or calculate the voltage by integrating an electric current flowing through the electrical contact 119B over a period of time. The first voltage comparator 301 may be controllably activated or deactivated by the controller 310. The first voltage comparator 301 may be a continuous comparator. Namely, the first voltage comparator 301 may be configured to be activated continuously and monitor the voltage continuously. The first voltage comparator 301 may be a clocked comparator. The first threshold may be 5-10%, 10%-20%, 20-30%, 30-40% or 40-50% of the maximum voltage one incident particle of radiation may generate on the electric contact 119B. The maximum voltage may depend on the energy of the incident particle of radiation, the material of the radiation absorption layer 110, and other factors. For example, the first threshold may be 50 mV, 100 mV, 150 mV, or 200 mV.

The second voltage comparator 302 is configured to compare the voltage to a second threshold. The second voltage comparator 302 may be configured to monitor the voltage directly or calculate the voltage by integrating an electric current flowing through the diode or the electrical contact over a period of time. The second voltage comparator 302 may be a continuous comparator. The second voltage comparator 302 may be controllably activate or deactivated by the controller 310. When the second voltage comparator 302 is deactivated, the power consumption of the second voltage comparator 302 may be less than 1%, less than 5%, less than 10% or less than 20% of the power consumption when the second voltage comparator 302 is activated. The absolute value of the second threshold is greater than the absolute value of the first threshold. As used herein, the term "absolute value" or "modulus" |x| of a real number x is the non-negative value of x without regard to its sign. Namely, $$|x| = \begin{cases} x, \text{ if } x \geq 0 \\ -x, \text{ if } x \leq 0. \end{cases}$$

The second threshold may be 200%-300% of the first threshold. The second threshold may be at least 50% of the maximum voltage one incident particle of radiation may generate on the electric contact 119B. For example, the second threshold may be 100 mV, 150 mV, 200 mV, 250 mV or 300 mV. The second voltage comparator 302 and the first voltage comparator 301 may be the same component. Namely, the electronic system 121 may have one voltage comparator that can compare a voltage with two different thresholds at different times.

The first voltage comparator 301 or the second voltage comparator 302 may include one or more op-amps or any other suitable circuitry. The first voltage comparator 301 or the second voltage comparator 302 may have a high speed to allow the electronic system 121 to operate under a high flux of incident particles of radiation. However, having a high speed is often at the cost of power consumption.

The counter 320 is configured to register at least a number of particles of radiation incident on the pixel 150 encompassing the electric contact 119B. The counter 320 may be a software component (e.g., a number stored in a computer memory) or a hardware component (e.g., a 4017 IC and a 7490 IC).

The controller 310 may be a hardware component such as a microcontroller and a microprocessor. The controller 310 is configured to start a time delay from a time at which the first voltage comparator 301 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on whether the voltage of the cathode or the anode of the diode or which electrical contact is used. The controller 310 may be configured to keep deactivated the second voltage comparator 302, the counter 320 and any other circuits the operation of the first voltage comparator 301 does not require, before the time at which the first voltage comparator 301 determines that the absolute value of the voltage equals or exceeds the absolute value of the first threshold. The time delay may expire before or after the voltage becomes stable, i.e., the rate of change of the voltage is substantially zero. The phase "the rate of change of the voltage is substantially zero" means that temporal change of the voltage is less than 0.1%/ns. The phase "the rate of change of the voltage is substantially non-zero" means that temporal change of the voltage is at least 0.1%/ns.

The controller 310 may be configured to activate the second voltage comparator during (including the beginning and the expiration) the time delay. In an embodiment, the controller 310 is configured to activate the second voltage comparator at the beginning of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 310 itself may be deactivated until the output of the first voltage comparator 301 activates the controller 310 when the absolute value of the voltage equals or exceeds the absolute value of the first threshold.

The controller 310 may be configured to cause the number registered by the counter 320 to increase by one, if, during the time delay, the second voltage comparator 302 determines that the absolute value of the voltage equals or exceeds the absolute value of the second threshold.

The controller 310 may be configured to cause the optional voltmeter 306 to measure the voltage upon expiration of the time delay. The controller 310 may be configured to connect the electric contact 119B to an electrical ground, so as to reset the voltage and discharge any charge carriers accumulated on the electric contact 119B. In an embodiment, the electric contact 119B is connected to an electrical ground after the expiration of the time delay. In an embodiment, the electric contact 119B is connected to an electrical ground for a finite reset time period. The controller 310 may connect the electric contact 119B to the electrical ground by controlling the switch 305. The switch may be a transistor such as a field-effect transistor (FET).

In an embodiment, the system 121 has no analog filter network (e.g., a RC network). In an embodiment, the system 121 has no analog circuitry.

The voltmeter 306 may feed the voltage it measures to the controller 310 as an analog or digital signal.

The electronic system 121 may include an integrator 309 electrically connected to the electric contact 119B, wherein the integrator is configured to collect charge carriers from the electric contact 119B. The integrator 309 can include a capacitor in the feedback path of an amplifier. The amplifier configured as such is called a capacitive transimpedance amplifier (CTIA). CTIA has high dynamic range by keeping the amplifier from saturating and improves the signal-to-noise ratio by limiting the bandwidth in the signal path. Charge carriers from the electric contact 119B accumulate on the capacitor over a period of time ("integration period"). After the integration period has expired, the capacitor voltage is sampled and then reset by a reset switch. The integrator 309 can include a capacitor directly connected to the electric contact 119B.

Figure 19:
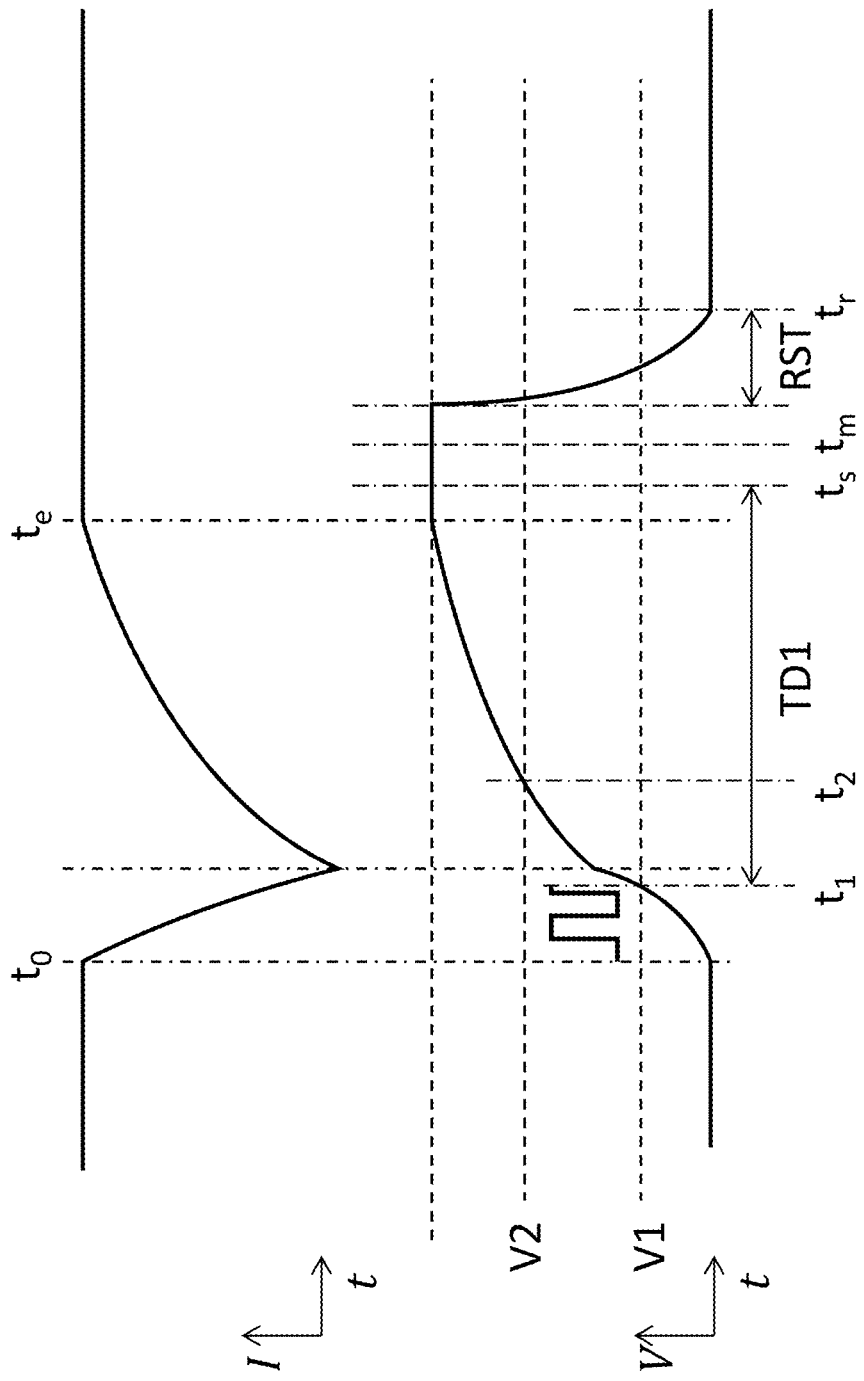
FIG. 19 schematically shows a temporal change of the electric current flowing through an electrode (upper curve) of a diode or an electric contact of a resistor of a radiation absorption layer exposed to radiation, the electric current caused by charge carriers generated by a radiation particle incident on the radiation absorption layer, and a corresponding temporal change of the voltage of the electrode (lower curve), according to an embodiment.

FIG. 19 schematically shows a temporal change of the electric current flowing through the electric contact 119B (upper curve) caused by charge carriers generated by a particle of radiation incident on the pixel 150 encompassing the electric contact 119B, and a corresponding temporal change of the voltage of the electric contact 119B (lower curve). The voltage may be an integral of the electric current with respect to time. At time to, the particle of radiation hits pixel 150, charge carriers start being generated in the pixel 150, electric current starts to flow through the electric contact 119B, and the absolute value of the voltage of the electric contact 119B starts to increase. At time $t_1$, the first voltage comparator 301 determines that the absolute value of the voltage equals or exceeds the absolute value of the first threshold V1, and the controller 310 starts the time delay TD1 and the controller 310 may deactivate the first voltage comparator 301 at the beginning of TD1. If the controller 310 is deactivated before $t_1$, the controller 310 is activated at $t_1$. During TD1, the controller 310 activates the second voltage comparator 302. The term "during" a time delay as used here means the beginning and the expiration (i.e., the end) and any time in between. For example, the controller 310 may activate the second voltage comparator 302 at the expiration of TD1. If during TD1, the second voltage comparator 302 determines that the absolute value of the voltage equals or exceeds the absolute value of the second threshold V2 at time $t_2$, the controller 310 waits for stabilization of the voltage to stabilize. The voltage stabilizes at time $t_e$, when all charge carriers generated by the particle of radiation drift out of the radiation absorption layer 110. At time $t_s$, the time delay TD1 expires. At or after time $t_e$, the controller 310 causes the voltmeter 306 to digitize the voltage and determines which bin the energy of the particle of radiation falls in. The controller 310 then causes the number registered by the counter 320 corresponding to the bin to increase by one. In the example of FIG. 9, time $t_s$ is after time $t_e$; namely TD1 expires after all charge carriers generated by the particle of radiation drift out of the radiation absorption layer 110. If time $t_e$ cannot be easily measured, TD1 can be empirically chosen to allow sufficient time to collect essentially all charge carriers generated by a particle of radiation but not too long to risk have another incident particle of radiation. Namely, TD1 can be empirically chosen so that time $t_s$ is empirically after time $t_e$. Time $t_s$ is not necessarily after time $t_e$ because the controller 310 may disregard TD1 once V2 is reached and wait for time $t_e$. The rate of change of the difference between the voltage and the contribution to the voltage by the dark current is thus substantially zero at $t_e$. The controller 310 may be configured to deactivate the second voltage comparator 302 at expiration of TD1 or at $t_2$, or any time in between.

The voltage at time $t_e$ is proportional to the amount of charge carriers generated by the particle of radiation, which relates to the energy of the particle of radiation. The controller 310 may be configured to determine the energy of the particle of radiation, using the voltmeter 306.

After TD1 expires or digitization by the voltmeter 306, whichever later, the controller 310 connects the electric contact 119B to an electric ground for a reset period RST to allow charge carriers accumulated on the electric contact 119B to flow to the ground and reset the voltage. After RST, the electronic system 121 is ready to detect another incident particle of radiation. If the first voltage comparator 301 has been deactivated, the controller 310 can activate it at any time before RST expires. If the controller 310 has been deactivated, it may be activated before RST expires.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:
1. A system comprising:
a radiation source;
a marker;
a first image sensor; and
a second image sensor;
wherein the first image sensor is configured to capture images of the marker;
wherein the second image sensor is configured to move between a first position relative to the radiation source and a second position relative to the radiation source;
wherein the second image sensor is configured to capture, with radiation from the radiation source, a first set of images of portions of a scene when the second image sensor is at the first position relative to the radiation source;
wherein the second image sensor is configured to capture, with the radiation from the radiation source, a second set of images of portions of the scene when the second image sensor is at the second position relative to the radiation source;
wherein the second image sensor and the radiation source are configured to collectively rotate relative to the scene;
wherein the second image sensor is configured to form an image of the scene by selecting an image from the first set based on the images of the marker and selecting an image from the second set based on the images of the marker, and stitching the image selected from the first set and the image selected from the second set.

2. The system of claim 1, wherein the marker is stationary relative to the scene; and wherein a relative position of the first image sensor with respect to the radiation source is fixed.

3. The system of claim 1, wherein the first image sensor is stationary relative to the scene; and wherein a relative position of the marker with respect to the radiation source is fixed.

4. The system of claim 1, wherein the second image sensor is configured to move between the first position relative to the radiation source and the second position relative to the radiation source by translating along a first direction relative to the radiation source.

5. The system of claim 4, wherein the first direction is parallel to a radiation-receiving surface of the second image sensor.

6. The system of claim 4, wherein the second image sensor is configured to move between the first position relative to the radiation source and the second position relative to the radiation source by translating along a second direction relative to the radiation source; wherein the second direction is different from the first direction.

7. The system of claim 1, wherein the second image sensor is configured to move between the first position relative to the radiation source and the second position relative to the radiation source by rotating about a first axis relative to the radiation source.

8. The system of claim 7, wherein the second image sensor is configured to move between the first position relative to the radiation source and the second position relative to the radiation source by rotating about a second axis relative to the radiation source; wherein the second axis is different from the first axis.

9. The system of claim 7, wherein the radiation source is on the first axis.

10. The system of claim 1, wherein the second image sensor and the radiation source are configured to collectively rotate relative to the scene about one or more axes.

11. The system of claim 10, wherein at least one of the one or more axes is on the second image sensor.

12. The system of claim 1, wherein a first rotational position which the radiation source is at when the image selected from the first set is captured and a second rotational position which the radiation source is at when the image selected from the second set is captured are the same.

13. The system of claim 1, wherein the images of the marker comprise a first image of the marker and a second image of the marker;
wherein rotational positions which the radiation source is at when the image selected from the first set is captured and when the first image of the marker is captured are the same;
wherein rotational positions which the radiation source is at when the image selected from the second set is captured and when the second image of the marker is captured are the same;
wherein the first image of the marker and the second image of the marker are identical.

14. The system of claim 1, wherein the second image sensor comprises a first radiation detector and a second radiation detector.

15. The system of claim 14, wherein the first radiation detector and the second radiation detector respectively comprise a planar surface configured to receive the radiation; wherein the planar surface of the first radiation detector and the planar surface of the second radiation detector are not coplanar.

16. The system of claim 15, wherein the first radiation detector and the second radiation detector are configured to move relative to the radiation source by translating along a first direction relative to the radiation source.

17. The system of claim 16, wherein the first direction is parallel to the planar surface of the first radiation detector but not parallel to the planar surface of the second radiation detector.

18. The system of claim 16, wherein the first radiation detector and the second radiation detector are configured to move relative to the radiation source by translating along a second direction relative to the radiation source; wherein the second direction is different from the first direction.

19. The system of claim 14, wherein the first radiation detector and the second radiation detector are configured to move relative to the radiation source by rotating about a first axis relative to the radiation source.

20. The system of claim 19, wherein the first radiation detector and the second radiation detector are configured to move relative to the radiation source by rotating about a second axis relative to the radiation source; wherein the second axis is different from the first axis.

21. The system of claim 19, wherein the radiation source is on the first axis.

22. A method comprising:
when a radiation source is at a first rotational position relative to a scene, capturing an image of first portions of the scene with radiation from the radiation source and capturing a first image of a marker;
when the radiation source is at a second rotational position relative to the scene, capturing an image of second portions of the scene with the radiation from the radiation source and capturing a second image of the marker;
determining whether the first rotational position and the second rotational position are the same based on the first image of the marker and the second image of the marker;
upon determining that the first rotational position and the second rotational position are the same, forming an image of the scene by stitching the image of the first portions and the image of the second portions.

23. The method of claim 22, wherein the marker is stationary relative to the scene; wherein the first image of the marker and the second image of the marker are captured by a first image sensor whose relative position with respect to the radiation source is fixed.

24. The method of claim 22, wherein the first image of the marker and the second image of the marker are captured by a first image sensor that is stationary relative to the scene; wherein a relative position of the marker with respect to the radiation source is fixed.

25. The method of claim 22, wherein the image of the first portions of the scene is captured by a second image sensor when the second image sensor is at a first position relative to the radiation source; wherein the image of the second portions of the scene is captured by the second image sensor when the second image sensor is at a second position relative to the radiation source.

26. The method of claim 25, wherein the second image sensor and the radiation source are configured to collectively rotate relative to the scene.

27. The method of claim 22, wherein determining whether the first rotational position and the second rotational position are the same based on the first image of the marker and the second image of the marker comprises: determining the first rotational position based on the first image of the marker and determining the second rotational position based on the second image of the marker.

28. The method of claim 22, determining whether the first rotational position and the second rotational position are the same based on the first image of the marker and the second image of the marker comprises: determining whether the first image of the marker and the second image of the marker are identical.

\* \* \* \* \*